US010918433B2

(12) United States Patent
Konesky et al.

(10) Patent No.: US 10,918,433 B2
(45) Date of Patent: Feb. 16, 2021

(54) DEVICES, SYSTEMS AND METHODS FOR ENHANCING PHYSIOLOGICAL EFFECTIVENESS OF MEDICAL COLD PLASMA DISCHARGES

(71) Applicant: Bovie Medical Corporation, Clearwater, FL (US)

(72) Inventors: Gregory A. Konesky, Hampton Bays, NY (US); Claes Fredrik Jonsson, Redington Beach, FL (US)

(73) Assignee: Apyx Medical Corporation, Clearwater, FL (US)

( * ) Notice: Subject to any disclaimer, the term of this patent is extended or adjusted under 35 U.S.C. 154(b) by 440 days.

(21) Appl. No.: 15/717,643

(22) Filed: Sep. 27, 2017

(65) Prior Publication Data
US 2018/0085155 A1 Mar. 29, 2018

Related U.S. Application Data

(60) Provisional application No. 62/400,251, filed on Sep. 27, 2016.

(51) Int. Cl.
*A61B 18/04* (2006.01)
*A61B 18/14* (2006.01)
(Continued)

(52) U.S. Cl.
CPC ........ *A61B 18/042* (2013.01); *A61B 18/1206* (2013.01); *A61B 18/14* (2013.01);
(Continued)

(58) Field of Classification Search
CPC ... A61B 18/042; A61B 18/1206; A61B 18/14; A61B 2018/00583; A61B 2018/122; A61B 2018/1475
See application file for complete search history.

(56) References Cited

U.S. PATENT DOCUMENTS

| | | | |
|---|---|---|---|
| 1,889,609 | A | 11/1932 | Arthur |
| 2,835,254 | A | 5/1958 | Coles |

(Continued)

FOREIGN PATENT DOCUMENTS

| | | |
|---|---|---|
| CN | 101134203 A | 3/2008 |
| CN | 103537245 B | 11/2015 |

(Continued)

*Primary Examiner* — Daniel W Fowler
*Assistant Examiner* — Tigist S Demie
(74) *Attorney, Agent, or Firm* — Gerald Hespos; Michael Porco; Matthew Hespos

(57) ABSTRACT

An electrosurgical apparatus for generating a plasma discharge beam is provided. In one aspect, the electrosurgical apparatus includes a first fluid flow housing, a second fluid flow housing, and an electrode. A first gas is provided to the distal end of the first fluid flow housing, where the electrode is energized to ionize the first gas and generate a plasma discharge beam. A second gas is provided to the distal end of the second fluid flow housing, where the distal end of the second fluid flow housing injects the second gas into the plasma discharge beam. In another aspect, the electrosurgical apparatus includes a single fluid flow housing having an external electrode and an internal electrode. In another aspect, the electrosurgical apparatus includes a transformer assembly having a plurality of serially-connected transformers.

15 Claims, 18 Drawing Sheets

(51) Int. Cl.
*A61B 18/12* (2006.01)
*A61B 18/00* (2006.01)

(52) U.S. Cl.
CPC .............. *A61B 2018/00583* (2013.01); *A61B 2018/122* (2013.01); *A61B 2018/1475* (2013.01)

(56) References Cited

U.S. PATENT DOCUMENTS

| | | | |
|---|---|---|---|
| 3,299,384 A | | 1/1967 | Hua-Tung |
| 3,434,476 A | * | 3/1969 | Shaw .................. A61B 18/042 606/22 |
| 3,577,030 A | | 5/1971 | Cusick et al. |
| 3,601,126 A | | 8/1971 | Estes |
| 3,949,266 A | | 4/1976 | Vogts et al. |
| 3,952,748 A | * | 4/1976 | Kaliher .................. A61B 18/12 606/37 |
| 3,970,088 A | | 7/1976 | Morrison |
| 3,987,795 A | | 10/1976 | Morrison |
| 4,040,426 A | | 8/1977 | Morrison, Jr. |
| 4,041,952 A | | 8/1977 | Morrison, Jr. et al. |
| 4,043,342 A | | 8/1977 | Morrison, Jr. |
| 4,060,088 A | | 11/1977 | Morrison, Jr. et al. |
| 4,255,735 A | | 3/1981 | Liautaud |
| 4,429,694 A | | 2/1984 | McGreevy |
| 4,492,231 A | | 1/1985 | Auth |
| 4,547,721 A | | 10/1985 | Drapp |
| 4,559,943 A | | 12/1985 | Bowers |
| 4,781,175 A | | 11/1988 | McGreevy et al. |
| 4,818,916 A | | 4/1989 | Morrisroe |
| 4,887,005 A | | 12/1989 | Rough et al. |
| 4,890,610 A | | 1/1990 | Kirwan et al. |
| 4,897,285 A | | 1/1990 | Wilhelm |
| 4,901,719 A | | 2/1990 | Trenconsky et al. |
| 4,901,720 A | | 2/1990 | Bertrand |
| 4,999,597 A | | 3/1991 | Gaynor |
| 5,088,997 A | | 2/1992 | Delahuerga et al. |
| 5,302,881 A | | 4/1994 | O'Loughlin |
| 5,325,019 A | | 6/1994 | Miller et al. |
| 5,669,904 A | | 9/1997 | Platt, Jr. et al. |
| 5,710,486 A | | 1/1998 | Ye et al. |
| 5,717,293 A | | 2/1998 | Sellers |
| 5,776,092 A | | 7/1998 | Farin et al. |
| 5,801,489 A | | 9/1998 | Chism, Jr. et al. |
| 5,815,047 A | | 9/1998 | Sorensen et al. |
| 5,917,286 A | | 6/1999 | Scholl et al. |
| 6,046,546 A | | 4/2000 | Porter et al. |
| 6,099,525 A | * | 8/2000 | Cosmescu .............. A61B 18/00 604/35 |
| 6,154,376 A | | 11/2000 | Dan-Harry |
| 6,170,668 B1 | | 1/2001 | Babko-Malyi |
| 6,181,068 B1 | | 1/2001 | Hur et al. |
| 6,213,999 B1 | | 4/2001 | Platt, Jr. et al. |
| 6,222,321 B1 | | 4/2001 | Scholl et al. |
| 6,262,538 B1 | | 7/2001 | Keller |
| 6,492,951 B1 | | 12/2002 | Harris et al. |
| 6,529,389 B2 | | 3/2003 | Perlick et al. |
| 6,627,163 B1 | | 9/2003 | Awakowicz et al. |
| 6,764,658 B2 | | 7/2004 | Denes et al. |
| 6,807,069 B2 | | 10/2004 | Nieminen et al. |
| 6,852,112 B2 | | 2/2005 | Platt |
| 7,070,144 B1 | | 7/2006 | DiCocco et al. |
| 7,275,013 B1 | | 9/2007 | Mathis et al. |
| 7,316,682 B2 | | 1/2008 | Konesky |
| 7,615,933 B2 | | 11/2009 | Hooke et al. |
| 7,630,774 B2 | | 12/2009 | Karni et al. |
| 7,913,351 B2 | | 3/2011 | Moriya |
| 7,928,338 B2 | | 4/2011 | Suslov |
| 8,057,468 B2 | | 11/2011 | Konesky |
| 8,267,884 B1 | | 9/2012 | Hicks |
| 8,377,388 B2 | | 2/2013 | Konesky |
| 8,383,038 B2 | | 2/2013 | Kitano |
| 8,409,190 B2 | | 4/2013 | Konesky et al. |
| 8,795,265 B2 | | 8/2014 | Konesky et al. |
| 8,802,022 B2 | | 8/2014 | Konesky |
| 9,060,765 B2 | | 6/2015 | Rencher et al. |
| 9,119,284 B2 | | 8/2015 | Sanematsu |
| 9,144,453 B2 | | 9/2015 | Rencher et al. |
| 9,649,143 B2 | | 5/2017 | Konesky et al. |
| 2004/0044342 A1 | * | 3/2004 | Mackay .............. A61B 18/042 606/45 |
| 2004/0116918 A1 | | 6/2004 | Konesky |
| 2005/0118350 A1 | * | 6/2005 | Koulik .................. A61B 18/042 427/535 |
| 2005/0187542 A1 | | 8/2005 | Auge et al. |
| 2005/0234442 A1 | | 10/2005 | Spears |
| 2006/0005545 A1 | | 1/2006 | Samimy et al. |
| 2006/0224154 A1 | | 10/2006 | Shadduck et al. |
| 2007/0089795 A1 | | 4/2007 | Jacob |
| 2008/0108985 A1 | | 5/2008 | Konesky |
| 2008/0193329 A1 | | 8/2008 | Akishev et al. |
| 2008/0302767 A1 | | 12/2008 | Yamaguchi et al. |
| 2009/0024122 A1 | | 1/2009 | Fischer |
| 2010/0021340 A1 | | 1/2010 | Buske et al. |
| 2011/0071517 A1 | | 3/2011 | Konesky et al. |
| 2011/0301412 A1 | | 12/2011 | Cho |
| 2012/0065635 A1 | | 3/2012 | Konesky |
| 2012/0116397 A1 | | 5/2012 | Rencher et al. |
| 2012/0172789 A1 | | 7/2012 | Fischer et al. |
| 2014/0005665 A1 | | 1/2014 | Konesky et al. |
| 2014/0316403 A1 | | 10/2014 | Konesky et al. |
| 2014/0341786 A1 | | 11/2014 | Konesky |
| 2015/0132711 A1 | | 5/2015 | Mason |
| 2016/0287310 A1 | | 10/2016 | Nettesheim et al. |
| 2018/0085155 A1 | | 3/2018 | Konesky et al. |
| 2019/0254734 A1 | | 8/2019 | Konesky |

FOREIGN PATENT DOCUMENTS

| | | |
|---|---|---|
| DE | 102013113941 | 6/2015 |
| DE | 102013113941 A1 | 6/2015 |
| EP | 0765638 | 4/1997 |
| EP | 0765638 A1 | 4/1997 |
| JP | 2007305845 A | 11/2007 |
| JP | 2008053661 | 3/2008 |
| JP | 2008053661 A | 3/2008 |
| WO | 2006100030 A1 | 9/2006 |
| WO | 2007071720 A1 | 6/2007 |
| WO | WO2007071720 | 6/2007 |
| WO | 2011029573 A1 | 3/2011 |
| WO | WO2011029573 | 3/2011 |
| WO | 2015059702 A1 | 4/2015 |
| WO | WO2015059702 | 4/2015 |
| WO | 2015087287 A1 | 6/2015 |
| WO | WO2015087287 | 6/2015 |

* cited by examiner

Straight downstream injection of a coaxial gas.

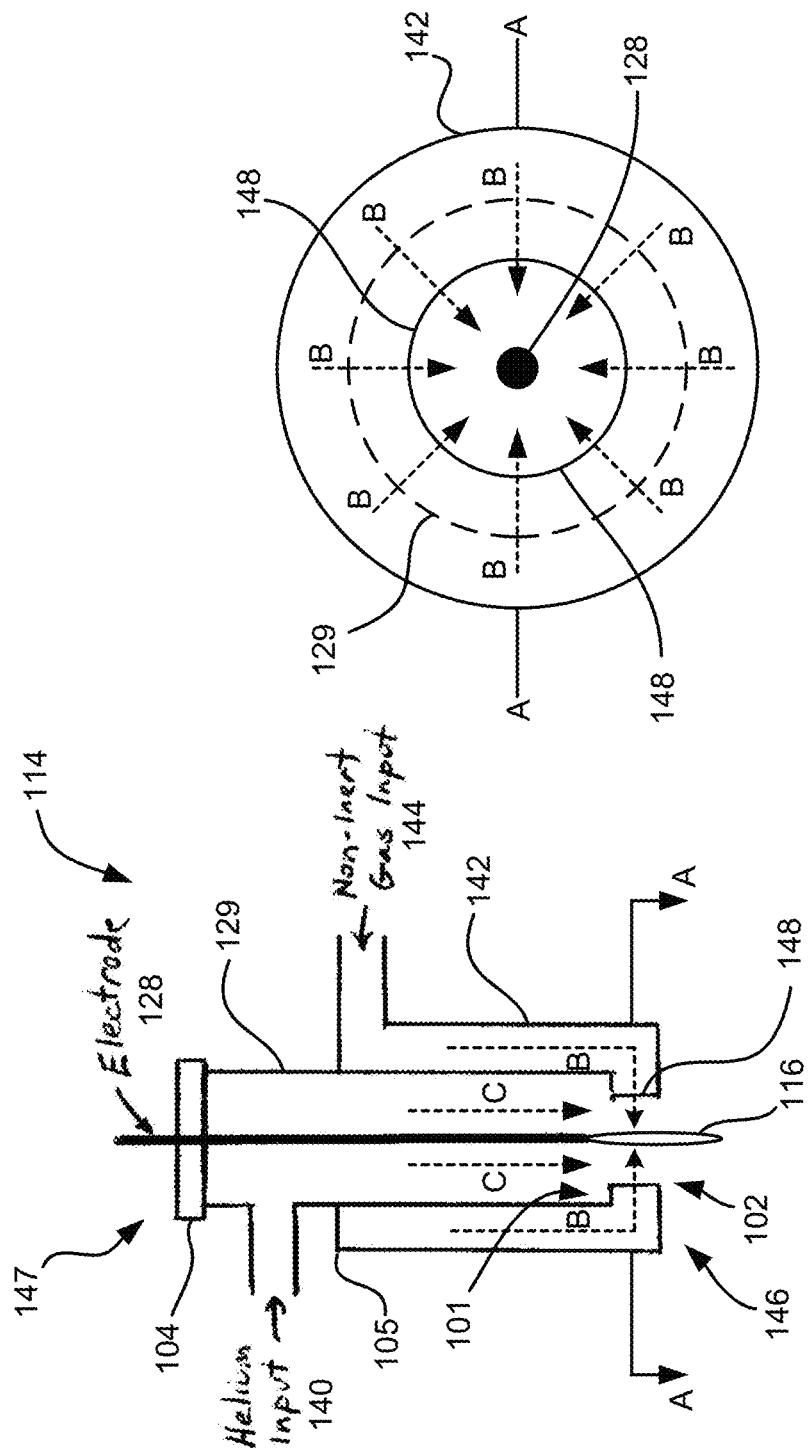

Local discharge applicator with two external electrodes

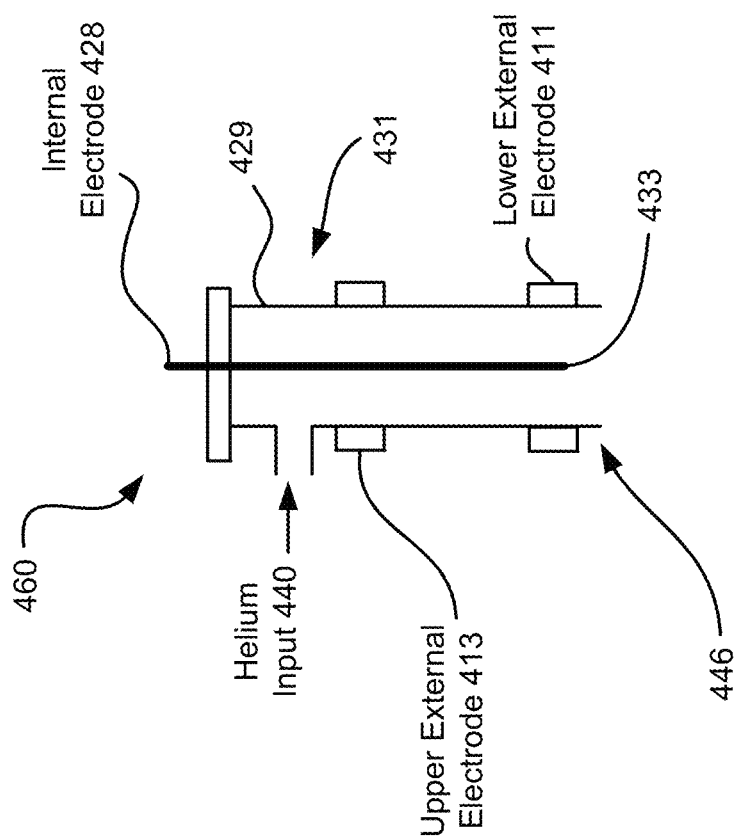
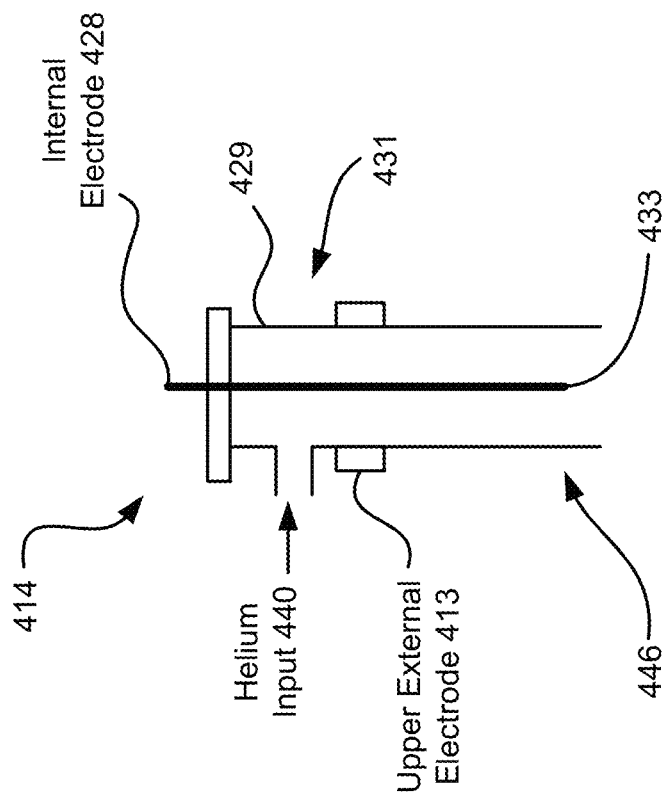
FIG. 9B
FIG. 9A (i)

(ii)

(iii)

Phase Combination (III)

Multi-stage approach to high voltage pulse generation

DEVICES, SYSTEMS AND METHODS FOR ENHANCING PHYSIOLOGICAL EFFECTIVENESS OF MEDICAL COLD PLASMA DISCHARGES

PRIORITY

This application claims priority to U.S. Provisional Patent Appl. No. 62/400,251, filed Sep. 27, 2016, entitled "DEVICES, SYSTEMS AND METHODS FOR ENHANCING PHYSIOLOGICAL EFFECTIVENESS OF MEDICAL COLD PLASMA DISCHARGES", the contents of which are hereby incorporated by reference.

BACKGROUND

Field

The present disclosure relates generally to electrosurgery and electrosurgical systems and apparatuses, and more particularly, to devices, systems and methods for enhancing physiological effectiveness of medical cold plasma discharges.

Description of the Related Art

High frequency electrical energy has been widely used in surgery and is commonly referred to as electrosurgical energy. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treated.

Electrosurgical systems that do not incorporate a source of regulated gas can ionize the ambient air between the active electrode and the patient. The plasma that is thereby created will conduct the electrosurgical energy to the patient, although the plasma arc will typically appear more spatially dispersed compared with systems that have a regulated flow of ionizable gas.

Atmospheric pressure discharge cold plasma applicators have found use in a variety of applications including surface sterilization, hemostasis, and ablation of tumors. Often, a simple surgical knife is used to excise the tissue in question, followed by the use of a cold plasma applicator for cauterization, sterilization, and hemostasis. Cold plasma beam applicators have been developed for both open and endoscopic procedures.

SUMMARY

Devices, systems and methods for enhancing physiological effectiveness of medical cold plasma discharges are provided.

In one aspect of the present disclosure, an electrosurgical apparatus is provided including: An electrosurgical apparatus comprising: a first fluid flow housing including a proximal end, a distal end, a first gas port, and a hollow interior, the first gas port configured to provide a first gas to the hollow interior, such that, the first gas flows through the hollow interior and is provided to the distal end of the first fluid flow housing; a second fluid flow housing including a proximal end, a distal end, a second gas port, and a hollow interior, the second fluid flow housing coaxially disposed over the first fluid flow housing, the second gas port configured to provide a second gas to the hollow interior of the second fluid flow housing, such that, the second gas flows through the hollow interior and is provided to the distal end of the second fluid flow housing; and an electrode disposed through the hollow interior of the first fluid flow housing, the electrode including a distal tip and configured to receive electrosurgical energy from an electrosurgical generator, such that, when the first gas passes over the distal tip of the electrode and the electrode receives electrosurgical energy, the first gas is at least partially ionized to generate a plasma discharge beam, the plasma discharge beam exiting the distal end of the first fluid flow housing, wherein the distal end of the second fluid flow housing is configured to inject the second gas into the plasma discharge beam.

In another aspect, the electrosurgical apparatus further includes: wherein the distal end of the second fluid flow housing is configured to inject the second gas into the plasma discharge beam in a direction perpendicular to a direction of flow of the first gas.

In another aspect, the electrosurgical apparatus further includes: wherein the distal end of the second fluid flow housing includes a gas output that extends in the direction perpendicular to the direction of flow of the first gas.

In another aspect, the electrosurgical apparatus further includes: wherein the gas output is configured as a circular slot.

In another aspect, the electrosurgical apparatus further includes: wherein the distal end of the second fluid flow housing includes at least one inlet vane, the at least one inlet vane configured to provide a tangential flow to the second gas as the second gas is injected into the plasma discharge beam.

In another aspect, the electrosurgical apparatus further includes: wherein the distal end of the second fluid flow housing includes a tapered tip, the tapered tip configured to increase the exit velocity of the second gas.

In another aspect, the electrosurgical apparatus further includes: wherein the tapered tip is configured in a conical shape.

In another aspect, the electrosurgical apparatus further includes: a transformer assembly, the transformer assembly including a plurality of transformers coupled in series, the transformer assembly configured to receive an input pulse from the electrosurgical generator and output an output pulse, the input pulse having a first voltage and a first pulse width and the output pulse having a second voltage and a second pulse width, the second voltage being higher than the first voltage and the second pulse width being narrower than the first pulse width.

In another aspect, the electrosurgical apparatus further includes: wherein the first gas is an inert gas and the second gas is a non-inert gas.

In another aspect, the electrosurgical apparatus further includes: wherein the first gas is helium.

In another aspect, the electrosurgical apparatus further includes: wherein the second gas is at least one of oxygen and/or nitrogen.

In another aspect, the electrosurgical apparatus further includes: wherein the second gas is a combination of oxygen and nitrogen.

In another aspect of the present disclosure, an electrosurgical apparatus is provided including: a fluid flow housing including a proximal end, a distal end, a gas port, and a hollow interior, the gas port configured to provide a gas to the hollow interior, such that, the gas flows through the hollow interior and is provided to the distal end of the fluid flow housing; and a first electrode and a second electrode, each electrode disposed exterior to the fluid flow housing, the first electrode disposed toward the proximal end of the fluid flow housing and the second electrode disposed toward the distal end of the fluid flow housing, wherein the first electrode and the second electrode are energized to pre-ionize the gas provided to the distal end of the fluid flow housing.

In another aspect, the electrosurgical apparatus further includes: wherein the first and second electrodes are each configured as ring electrodes, such that, the first electrode completely surrounds a proximal portion of the fluid flow housing and the second electrode completely surrounds a distal portion of the fluid flow housing.

In another aspect, the electrosurgical apparatus further includes: a third electrode centrally disposed through the hollow interior of the fluid flow housing, the third electrode configured to receive electrosurgical energy from an electrosurgical generator to generate a plasma discharge beam when the gas passes over a distal tip of the third electrode.

In another aspect, the electrosurgical apparatus further includes: wherein the first and second electrodes are operated at different electrical phase relationships than the third electrode to maintain an ionizing potential between the first and second electrodes and the third electrode.

In another aspect, the electrosurgical apparatus further includes: a transformer assembly, the transformer assembly including a plurality of transformers coupled in series, the transformer assembly configured to receive an input pulse from the electrosurgical generator and output an output pulse, the input pulse having a first voltage and a first pulse width and the output pulse having a second voltage and a second pulse width, the second voltage being higher than the first voltage and the second pulse width being narrower than the first pulse width, the output pulse provided to the third electrode.

In another aspect of the present disclosure, an electrosurgical apparatus is provided including: a housing; an electrode; a transformer assembly including a plurality of transformers coupled in series, each transformer configured to receive an input pulse having a first voltage and a first pulse width and output an output pulse having a second voltage and second pulse width, the second voltage being greater than the first voltage and the second pulse width being narrower than the first pulse width, wherein the transformer assembly is configured to receive a first input pulse from an electrosurgical generator and output a first output pulse having a higher voltage and narrower pulse width than the first input pulse, the first output pulse provided from the transformer assembly to the electrode.

In another aspect, the electrosurgical apparatus further includes: wherein each of the plurality of transformers is a saturable core transformer.

In another aspect, the electrosurgical apparatus further includes: wherein the core of each saturable core transformer is ring-shaped.

The electrosurgical apparatus of claim 19, wherein the core of each saturable core transformer is made of a ferrite material.

In another aspect of the present disclosure, an electrosurgical apparatus is provided including: a first fluid flow housing including a proximal end, a distal end, a gas port, and a hollow interior, the gas port configured to provide a first gas to the hollow interior, such that, the first gas flows through the hollow interior and is provided to the distal end of the first fluid flow housing, the hollow interior having a first diameter; a nozzle including a proximal end and a distal end, the proximal end of the nozzle coupled to the distal end of the first fluid flow housing, the nozzle further including a hollow interior and at least one secondary gas input disposed through an exterior portion of the nozzle and providing access to the hollow interior of the nozzle, the hollow interior including a throttle portion having a second diameter, the second diameter being smaller than the first diameter; and an electrode disposed through the hollow interior of the first fluid flow housing, the electrode including a distal tip and configured to receive electrosurgical energy from an electrosurgical generator, such that, when the first gas passes over the distal tip of the electrode and the electrode receives electrosurgical energy, the first gas is at least partially ionized to generate a plasma discharge beam, the plasma discharge beam exiting the distal end of the first fluid flow housing and extending through the hollow interior of the nozzle, such that, the plasma discharge beam exits the distal ends of the nozzle; wherein when the plasma discharge beam extends through the throttle portion of the nozzle, a pressure difference between the hollow interior of the nozzle and the exterior of the nozzle causes a second gas to be drawn into the hollow interior of the nozzle through the at least one secondary gas input and injected into the plasma discharge beam.

In another aspect, the electrosurgical apparatus further includes: wherein the at least one secondary gas input is configured to inject the second gas at the throttle portion.

In another aspect, the electrosurgical apparatus further includes: wherein the hollow interior of the nozzle further includes a converging portion and a diverging portion, the converging portion disposed adjacent to the throttle portion in a direction toward the proximal and of the nozzle, the diverging portion disposed adjacent to the throttle portion in a direction toward the distal end of the nozzle, wherein the converging portion is configured to gradually decrease a diameter of the hollow interior of the nozzle from the proximal end of the nozzle to the throttle portion, and wherein the diverging portion is configured to gradually increase the diameter of the hollow interior of the nozzle from the throttle portion to the distal end of the nozzle.

In another aspect, the electrosurgical apparatus further includes: wherein the at least one secondary gas input is configured to inject the second gas at the diverging portion.

In another aspect, the electrosurgical apparatus further includes: wherein the at least one secondary gas input is configured to inject the second gas in a direction perpendicular to the direction of flow of the first gas.

In another aspect, the electrosurgical apparatus further includes: wherein the second gas is ambient air exterior to the first fluid flow housing.

In another aspect, the electrosurgical apparatus further includes: a second fluid flow housing coaxially disposed around the first fluid flow housing, the second fluid flow housing including a second gas port and a hollow interior, the second gas port providing a second gas to the hollow interior of the second fluid flow housing, wherein when the plasma discharge beam extends through the throttle portion of the nozzle, a pressure difference between the hollow interior of the nozzle and hollow interior of the second fluid flow housing causes the second gas to be drawn into the hollow interior of the nozzle through the at least one secondary gas input and injected into the plasma discharge beam.

In another aspect, the electrosurgical apparatus further includes: wherein the first gas is an inert gas and the second gas is a non-inert gas.

BRIEF DESCRIPTION OF THE DRAWINGS

The above and other aspects, features, and advantages of the present disclosure will become more apparent in light of the following detailed description when taken in conjunction with the accompanying drawings in which:

FIG. 3A illustrates the plasma applicator shown in FIG. 2 with tangential injectors in accordance with the present disclosure;

FIG. 3B is a cross-section view of the plasma applicator shown in FIG. 3A taken along line A-A in accordance with another embodiment of the present disclosure;

FIG. 9A illustrates a direct discharge applicator with a combined internal electrode with a single external electrode in accordance with an embodiment of the present disclosure;

FIG. 9B illustrates a direct discharge applicator with a combined internal electrode with dual external electrodes in accordance with an embodiment of the present disclosure;

Figure 1:
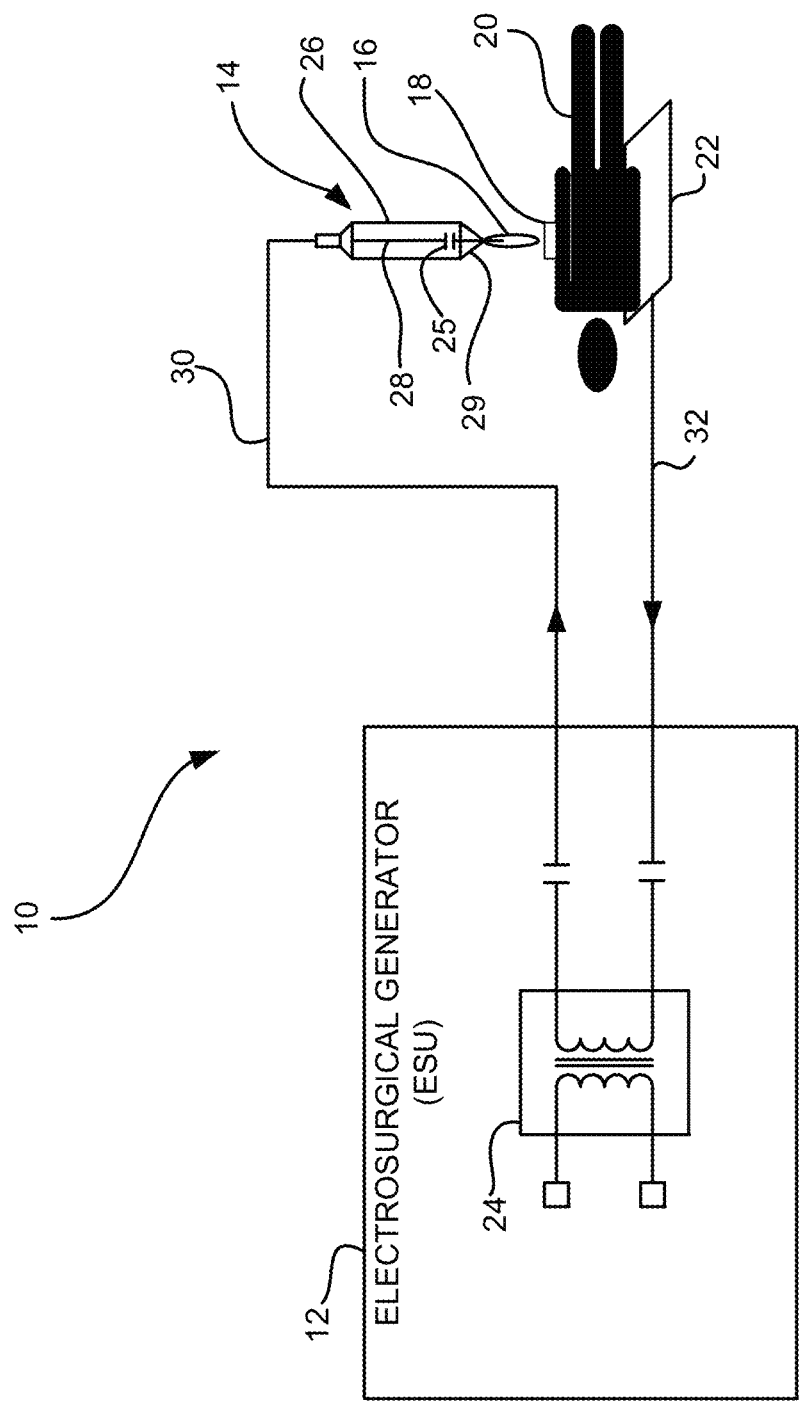
FIG. 1 is an illustration of an exemplary monopolar electrosurgical system in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

Atmospheric pressure cold plasma discharge beam jets are generally formed by one of two mechanisms. The first is referred to as a "local" discharge, where the primary plasma discharge is confined to the plasma applicator hand piece. The flowing carrier gas draws out an afterglow, which forms the visible beam emerging from the exit nozzle tip of the applicator hand piece. Such local discharge applicators typically have a ground ring around the outer periphery of the exit nozzle tip and complete the plasma discharge circuit within the hand piece.

The second type of cold plasma applicator has a centrally mounted electrode wire positioned down the axis of an insulating tube. An exemplary cold plasma applicator having a centrally mounted electrode wire is shown and described in commonly owned U.S. Pat. No. 7,316,682 to Konesky, the details of which will be described below in relation to FIG. 1. The wire may also be flattened into a cutting blade which, when retracted into the insulating tube, serves as an electrode. An exemplary cold plasma applicator having an electrode wire configured as a cutting blade is shown and described in commonly owned U.S. Pat. No. 9,060,765 to Rencher et al., the contents of which are incorporated by reference. Regardless of the applicator configuration, this electrode is held at high voltage and high frequency, typically from a few hundred to a few thousand volts, and several kilohertz to several megahertz, respectively. Inert carrier gas flowing through the tube, and over the wire, produces a luminous discharge path from the tip of this wire electrode to the target application site. The discharge path occurs directly from the exit tip of the applicator hand piece to the target application site, so is said to be a "direct" discharge applicator.

FIG. 1 shows an exemplary monopolar electrosurgical system generally indicated as 10 comprising an electrosurgical generator (ESU) generally indicated as 12 to generate power for the electrosurgical apparatus 10 and a cold plasma applicator or generator having a centrally mounted electrode wire generally indicated as 14 to generate and apply a plasma stream 16 to a surgical site or target area 18 on a patient 20 resting on a conductive plate or support surface 22. The electrosurgical generator 12 includes a transformer generally indicated as 24 including a primary and secondary coupled to an electrical source (not shown) to provide high frequency electrical energy to the cold plasma applicator 14. Typically, the electrosurgical generator 12 comprises an isolated floating potential not referenced to any potential. Thus, current flows between the active and return electrodes. If the output is not isolated, but referenced to "earth", current can flow to areas with ground potential. If the contact surface of these areas and the patient is relatively small, an undesirable burning can occur.

The cold plasma applicator 14 comprises a handpiece or holder 26 having an electrode 28 at least partially disposed within a fluid flow housing 29 and coupled to the transformer 24 to receive the high frequency electrical energy therefrom to at least partially ionize noble gas fed to the fluid flow housing 29 of the handpiece or holder 26 to generate or create the plasma stream 16. The high frequency electrical energy is fed from the secondary of the transformer 24 through an active conductor 30 to the electrode 28 (collectively active electrode) in the handpiece 26 to create the plasma stream 16 for application to the surgical site 18 on the patient 20. Furthermore, a current limiting capacitor 25 is provided in series with the electrode 28 to limit the amount of current being delivery to the patient 20.

The return path to the electrosurgical generator 12 is through the tissue and body fluid of the patient 20, the conductor plate or support member 22 and a return conductor 32 (collectively return electrode) to the secondary of the transformer 24 to complete the isolated, floating potential circuit.

In another embodiment, the electrosurgical generator 12 comprises an isolated non-floating potential not referenced to any potential. The plasma current flow back to the electrosurgical generator 12 is through the tissue and body fluid and the patient 20. From there, the return current circuit is completed through the combined external capacitance to the cold plasma applicator handpiece 26, surgeon and through displacement current. The capacitance is determined, among other things, by the physical size of the patient 20. Such an electrosurgical apparatus and generator are described in commonly owned U.S. Pat. No. 7,316,682 to Konesky, the contents of which are hereby incorporated by reference in its entirety.

It is to be appreciated that transformer 24 may be disposed in the cold plasma applicator handpiece 26, as will be described in various embodiments below. In this configuration, other transformers may be provided in the generator 12 for providing a proper voltage and current to the transformer in the handpiece, e.g., a step-down transformer, a step-up transformer or any combination thereof.

Atmospheric pressure cold plasma discharges achieve a desired physiological action through a concert of effects. These includes electron and ion bombardment, and the associated charge transfers, localized thermal effects, high electric fields, generation of radical species, and ultra-violet emissions. The contribution of a given effect to the overall physiological effectiveness can be enhanced through a variety of approaches, including carrier gas composition and method of introduction, applicator electrode locations, and methods of high voltage high frequency generation.

Helium is often the carrier gas of choice due to its high thermal conductivity and self-limiting potential for avalanche multiplication of the plasma discharge beam current. Both of these properties work together to provide a highly localized effect with minimal collateral damage to surrounding tissue. The high thermal conductivity of helium acts to carry away excess heat from the application site which would otherwise have the potential to damage surrounding tissue. Since helium only has two electrons, the potential for avalanche multiplication is limited, resulting in reduced, stable plasma beam currents. Consequently, when this beam current is dissipated in tissue surrounding the application site, the resulting ohmic heating is also reduced, again, limiting collateral tissue damage.

However, there may be circumstances where deeper tissue heating is desirable. These include skin resurfacing and wrinkle removal, disinfection of bulk infectious agents including biofilms, and bulk cancer cell treatment. If the plasma energy is only applied on the target surface, steep temperature gradients would be required to produce deep tissue heating, causing excessive and potentially damaging surface temperatures.

One method of increasing deliverable beam currents while maintaining the stable, self-limiting nature of a pure helium carrier gas is to utilize a mixture of inert gases. The additional gas atoms would have a much higher capacity for multiple electron loss (i.e., become more highly ionized) and so have a much higher current carrying capacity on a per-atom basis. Examples of these added gases include argon, krypton and xenon. Argon, with 18 electrons, would require significant ionization energy to remove more than just a few outer electrons, while krypton and xenon, with 36 and 54 electrons respectively, are much more easily multiply-ionized.

Note that with relatively small admixtures of these heavy inert gases (e.g., a few percent by volume), the average plasma beam gas temperature would not increase significantly, so the surface temperature of the application site would be essentially the same as if pure helium was being used. Another motivation for using only small percentages of admixed heavy inert gases is their high cost relative to helium.

In certain uses of cold plasma discharges, the production of radical species play an important role in the physiological effect, particularly in disinfection, sterilization, and cancer treatment applications. Radical species such as reactive oxygen species (ROS), reactive nitrogen species (RNS) and reactive oxy-nitrogen species (RONS) are typically generated by the interaction of atmospheric oxygen and nitrogen with the cold plasma discharge beam. Their production rate is limited, among other causes, by the diffusion rate of atmospheric components into the plasma beam.

The production rate of these radical species, and their associated physiological effectiveness, can be significantly improved by adding small amounts of oxygen, nitrogen, or a combination of the two to the inert carrier gas, typically on the order of a few volume percent.

However, in applicator topologies where an internal electrode is directly exposed to the ionized carrier gas, the presence of these non-inert ionized gases may result in significantly accelerated erosion if the electrode surface. This is especially true in the presence of ionized oxygen.

Figure 2:
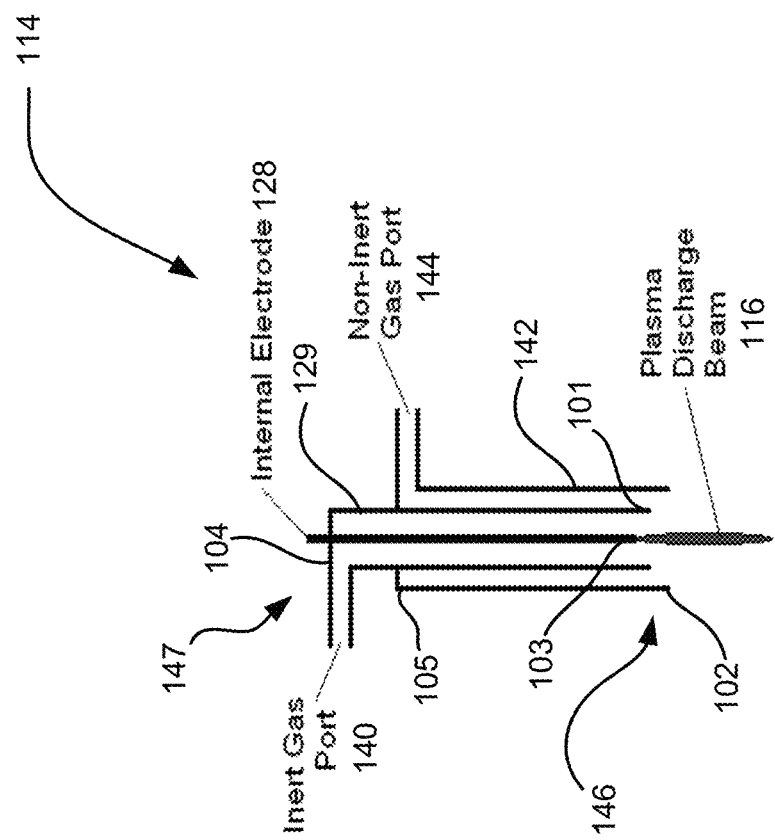
FIG. 2 illustrates an exemplary plasma applicator in accordance with an embodiment of the present disclosure.

To prevent this, oxygen or nitrogen, or potentially other non-inert gases, can be added to the plasma beam down stream of the internal electrode. FIG. 2 illustrates a coaxial configuration where the non-inert gas is added externally and coaxially to the plasma beam, while remaining down stream of the internal electrode. Referring to FIG. 2, applicator 114 is shown in accordance with the present disclosure. Applicator 114 includes a proximal end 147 and a distal end 146. Applicator 144 includes a fluid flow housing 129 for providing an inert gas to a distal end 101 of fluid flow housing 129. The fluid flow housing 129 receives the inert gas via an inert gas port 140. Gas port 140 may be disposed toward proximal end 104 of fluid flow housing 129. The inert gas may be provided from a gas source coupled to inert gas port 140. The inert gas provided via inert gas port 140 flows through hollow interior of fluid flow housing 129 and out of the distal end 101 of fluid flow housing 129.

Internal electrode 128 is disposed centrally in the fluid flow housing 129. Internal electrode 128 may be coupled to an electrosurgical generator disposed exterior to applicator 114. Internal electrode 128 is configured to receive electrosurgical energy (e.g., with high voltage and at high frequency) from the electrosurgical generator. Internal electrode 129 includes a distal tip 103, where distal end 101 of fluid flow housing 129 extends passed distal tip 103 of internal electrode 128.

A non-inert fluid flow housing 142 is coaxially disposed around the fluid flow housing 129 and is coupled to a non-inert gas source via non-inert gas port 144. Gas port 144 may be disposed toward proximal end 105 of fluid flow housing 142. Fluid flow housing 142 includes a hollow interior configured to carry non-inert gas provided via non-inert gas port 144 to the distal end 102 of fluid flow housing 142. It is to be appreciated that the hollow interior of fluid flow housing 142 is configured to contain the non-inert gas provided by non-inert gas port 144, such that, the non-inert gas does not enter the hollow interior of fluid flow housing 129.

A plasma discharge beam is generated when an inert gas flows through the hollow interior of fluid flow housing 129 and passes over the distal tip 103 of the electrode 128, when the electrode 128 is supplied with high voltage at a high frequency from an electrosurgical generator. The plasma discharge beam exits the distal end 101 of fluid flow housing 129. The non-inert gas is then injected into the plasma discharge beam 116 by providing the non-inert gas to the distal end 146 of the applicator 114 via the non-inert gas fluid flow housing 142. As shown in FIG. 2, the distal end 102 of fluid flow housing 142 extends passed the distal end 101 of fluid flow housing 129. In this way, the non-inert gas is only injected after the plasma discharge beam 116 has already been generated and is exiting the distal end 101 of fluid flow housing 129.

The distal end 102 of fluid flow housing 129 is configured to inject non-inert gas into the plasma discharge beam 116. As will be described below, the distal ends 101, 102 of housings 129, 142 may be modified in accordance with the present disclosure to enhance the injecting and mixing of the non-inert gas with the plasma discharge beam 116.

Introduction of these additional non-inert gases into the plasma discharge beam 129 can be further improved by injecting the non-inert gas(es) at an angle relative to the direction of flow of the carrier gas. For example, to FIGS. 3A and 3B an applicator 114 is shown in accordance with present disclosure. The design of the applicator 114 enhances the mixing of the added non-inert gases with the plasma beam 116 and its associated inert carrier gas flow. As shown in FIG. 3A, inert gas (e.g., helium) is provided via gas port 140 to the hollow interior of fluid flow housing 129. The inert gas flow in a direction C (shown in FIG. 3A) within the hollow interior of fluid flow housing 129. Non-inert gas is provided via gas port 144 into the hollow interior of fluid flow housing 142. The non-inert gas flows in a direction B (shown in FIG. 3A). In this embodiment, the distal end 102 of fluid flow housing 142 is configured to inject the non-inert gas at a right angle to the flow of the inert gas. In one embodiment, the non-inert gas fluid flow housing 142 is configured with a gas output 148 at the distal end 102 that extends perpendicularly to the direction of the flow of the inert gas (i.e., perpendicularly to direction C) in a direction toward the shared center of fluid flow housings 129, 142. As shown in FIG. 3B, in some embodiments, gas output 148 is configured as a circular slot that injects non-inert gas radially toward the shared center of fluid flow housings 129, 142 from all directions.

Figure 3C:
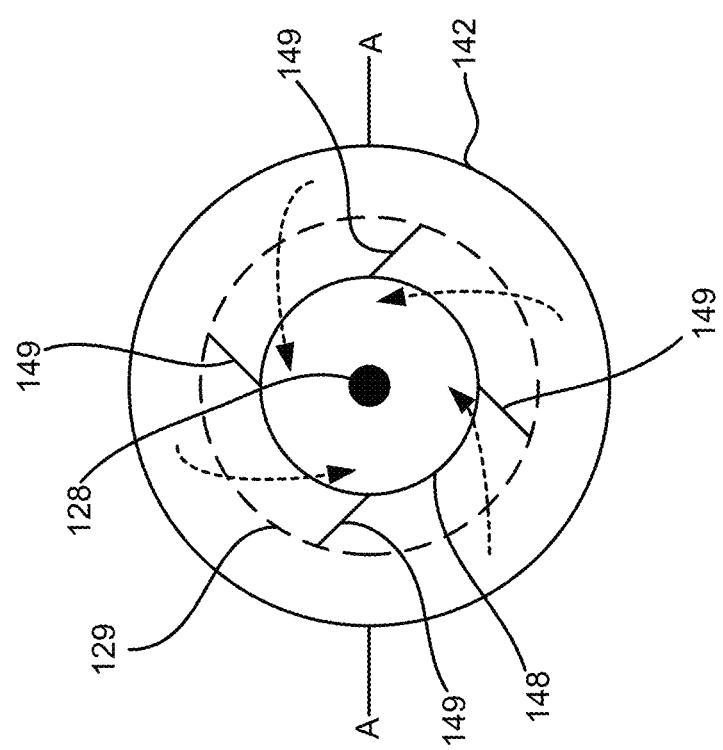
FIG. 3C is a cross-section view of a plasma applicator similar to the plasma applicator shown in FIG. 3A, including inlet vanes, in accordance with another embodiment of the present disclosure.

In some embodiments, one or more tilted inlet vanes may be disposed within the circular slot of gas output to introduce a tangential flow (i.e., a swirling or curling) of the non-inert gas as the non-inert gas is injected into the plasma discharge beam 116. For example, referring to FIG. 3C, one or more inlet vanes 149 are shown disposed in the circular slot of gas output 148, such that, inlet vanes 149 are downstream of electrode 128. Inlet vanes 149 are tilted or slanted (as shown in FIG. 3C) to create a tangential flow (i.e., a swirling or curling) of the non-inert gas with respect to the shared center of housings 129, 142 as the non-inert gas is injected into the plasma discharge beam 116 to further enhance injection and mixing. It is to be appreciated that although four inlet vanes 149 are shown in FIG. 3C, in other embodiments, applicator 114 may include any number of inlet vanes 149 (i.e., more or less than four inlet vanes).

Figure 4:
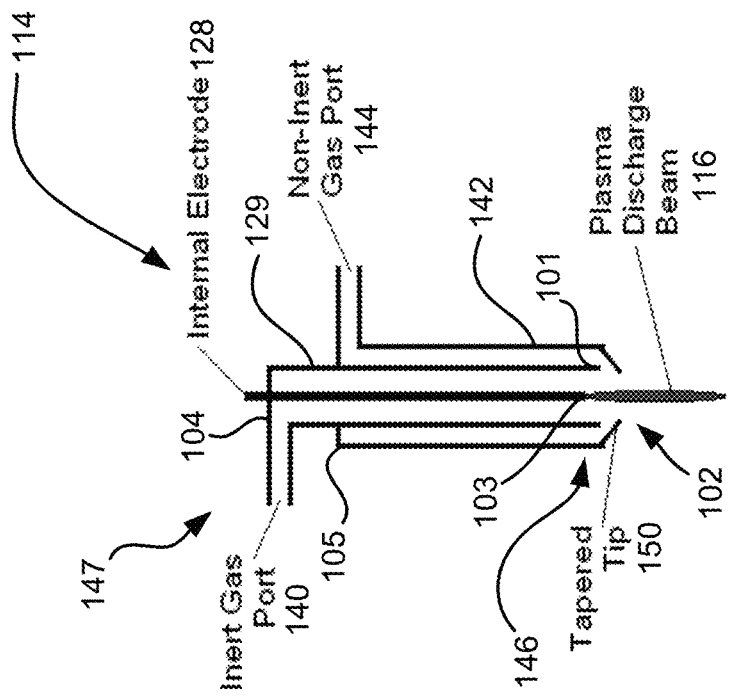
FIG. 4 illustrates the plasma applicator shown in FIG. 2 with a coaxial injector in accordance with another embodiment of the present disclosure.

Improved mixing of the non-inert gases can also be affected by tapering and reducing the exit diameter of the distal end 102 of external coaxial tube 142. For example, referring to FIG. 4. As shown in FIG. 4, the external coaxial tube (i.e., the non-inert fluid flow housing 142) can be configured with a tapered tip 150 at the distal end 102. The tapered tip may form a conical shape, where the opening of the tapered tip has a smaller diameter than the diameter of the non-inert fluid flow housing 142. In another embodiment, tapered tip 150 may be configured as a separate conical end piece that is attached and added to the distal end 102 of the non-inert fluid flow housing 142 to achieve the same effect. In either case, tapered tip 150 is configured to increase the exit velocity of the non-inert gas flow and improve turbulent mixing at the boundary of the coaxial gas flows. Furthermore, the tapered tip 150 is configured to inject the non-inert gas into the plasma discharge beam 116 at an angle, which also improves the mixing of the non-inert gas with the plasma discharge beam 116.

Enhanced mixing and injection of the non-inert gas into a plasma discharge beam may also be achieved by including a De Laval nozzle distal to the electrode tip of a plasma applicator. The De Laval nozzle is configured to take advantage of the Venturi effect to enhance the mixing and injection of the non-inert gas into the plasma discharge beam.

The Venturi effect states that when a constant volume flow of a fluid passes through a constricted area, the velocity of the fluid will increase and the static pressure of the fluid will decrease.

Figure 5A:
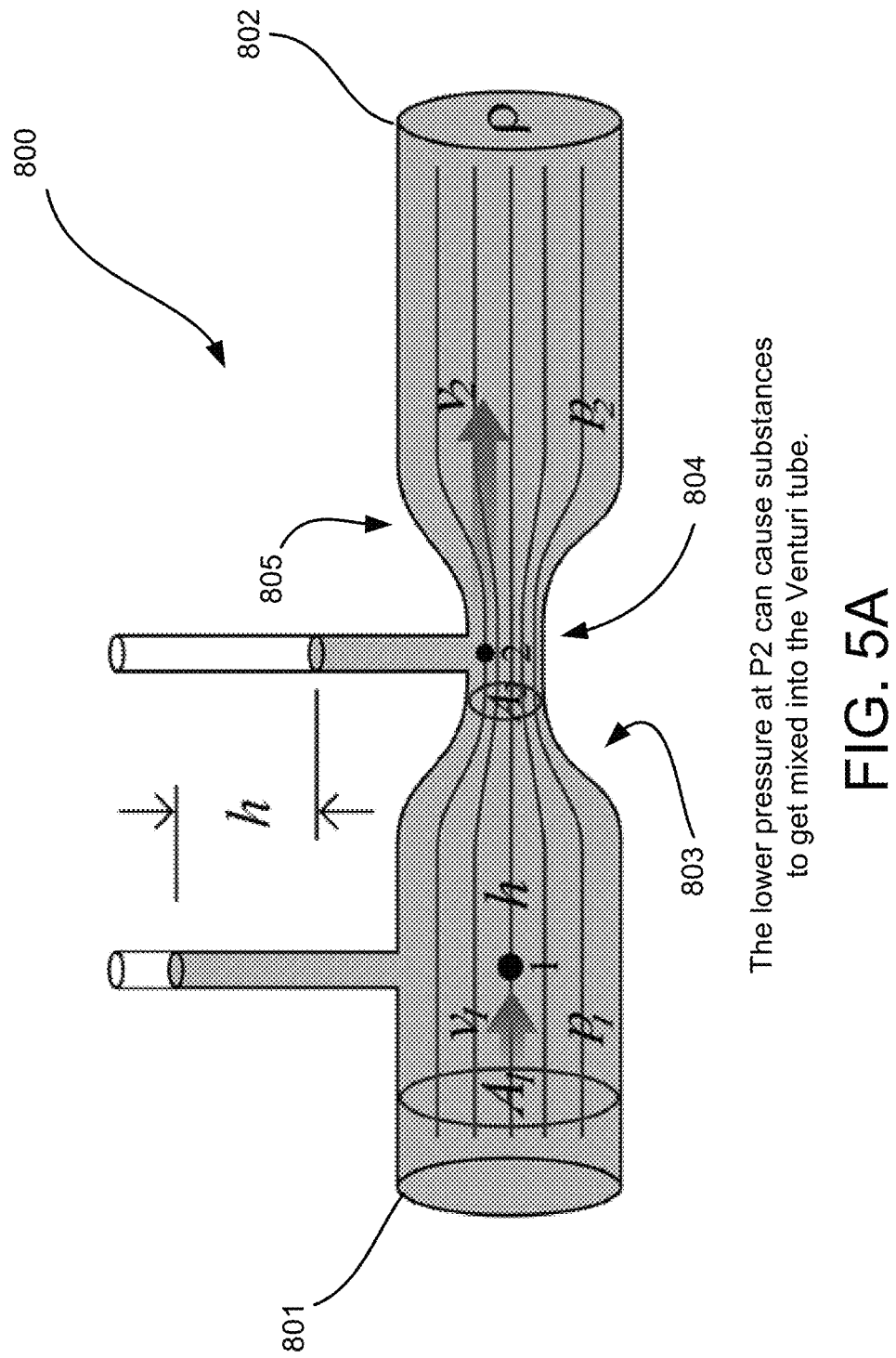
FIG. 5A illustrates a tube undergoing the Venturi effect in accordance with the present disclosure.

Referring to FIG. 5A a Venturi tube 800 is shown in accordance with the present disclosure. In tube 800, the fluid flows from end 801 to end 802 at a constant volume flow rate. Tube 800 includes a converging portion 803, a throat or throttle portion 804, and a diverging portion 805. To maintain constant volume flow rate, the fluid flowing through tube 800 must be moved at the same rate, despite the constricted space in the throttle portion 804 of tube 800. Therefore, the velocity of the fluid is increased. The velocity change will create a pressure change according to Bernoulli's principle, which states that within a specified flow field, a decrease in pressure occurs when there is an increase in velocity.

One application of Venturi tubes, such as tube 800, is mixing of liquids and/or gases. This is possible because the lower pressure inside the tube 800 creates a pressure difference between the device and its surrounding environment. As gas flows through the interior of tube 800 from end 801 to end 802, substances outside of the Venturi tube 800 (e.g., ambient air) are sucked into the low-pressure area (i.e., throttle portion 804), and gas and/or liquid components become mixed together within the tube 800.

Figure 5B:
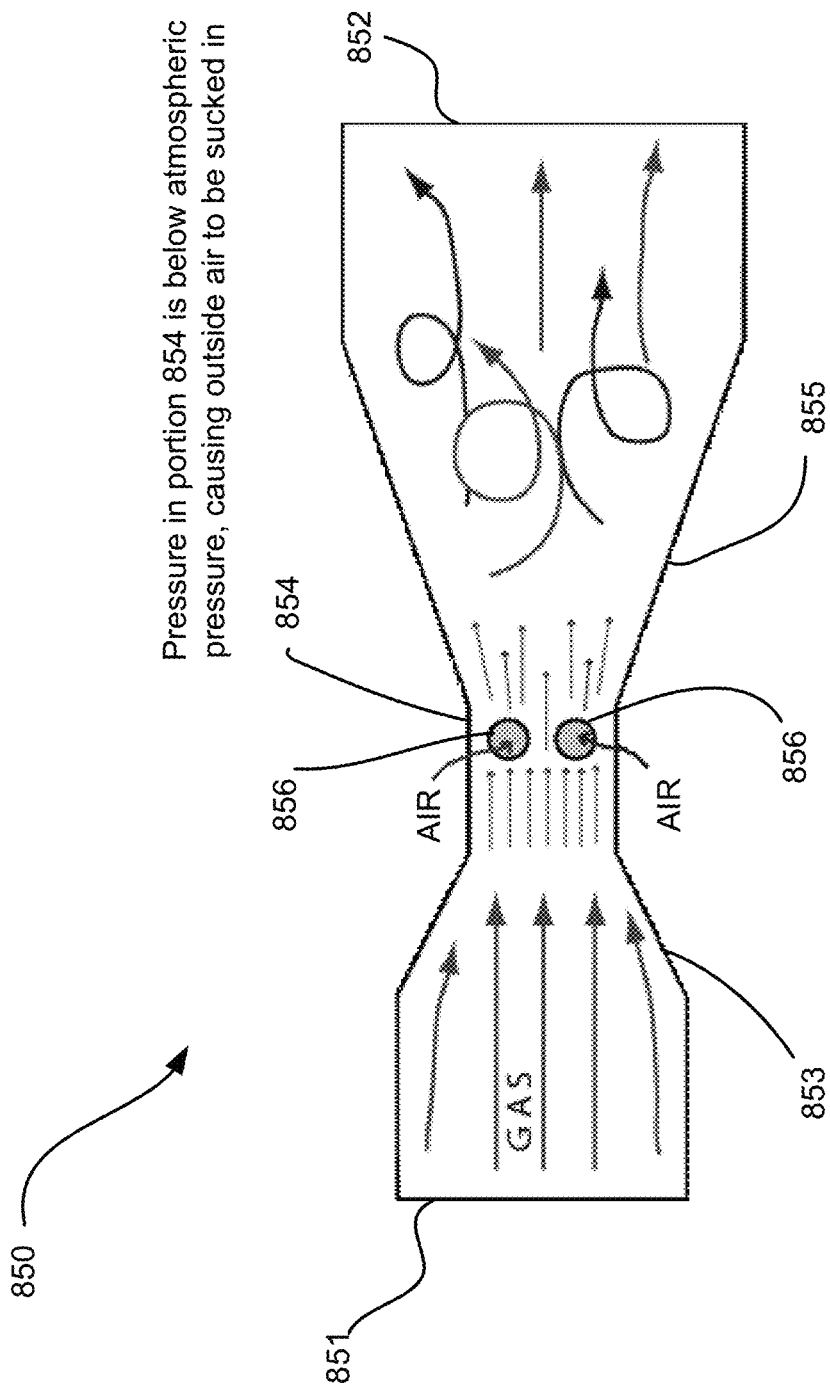
FIG. 5B illustrates a Venturi burner in accordance with the present disclosure.

Venturi burners are an example of a device that employs the Venturi effect. Referring to FIG. 5B, a Venturi burner 850 is shown. Venturi burner 850 include ends 851, 852, converging portion, 853, throttle portion 854. Throttle portion 854 includes one or more apertures 855, and diverging portion 856. The lower pressure inside the burner 850 creates a pressure difference between the interior of burner 850 and its surrounding environment. As gas and/or liquid flows from end 851 of burner 850 to end 852 of burner 850, substances outside of the burner 850, such as ambient air, are sucked into the throttle portion 854 via aperture 856, and the gas and/or liquid components from outside of the burner 850 become mixed with the gas and/or liquid flowing through the interior of the burner 850.

Figure 6B:
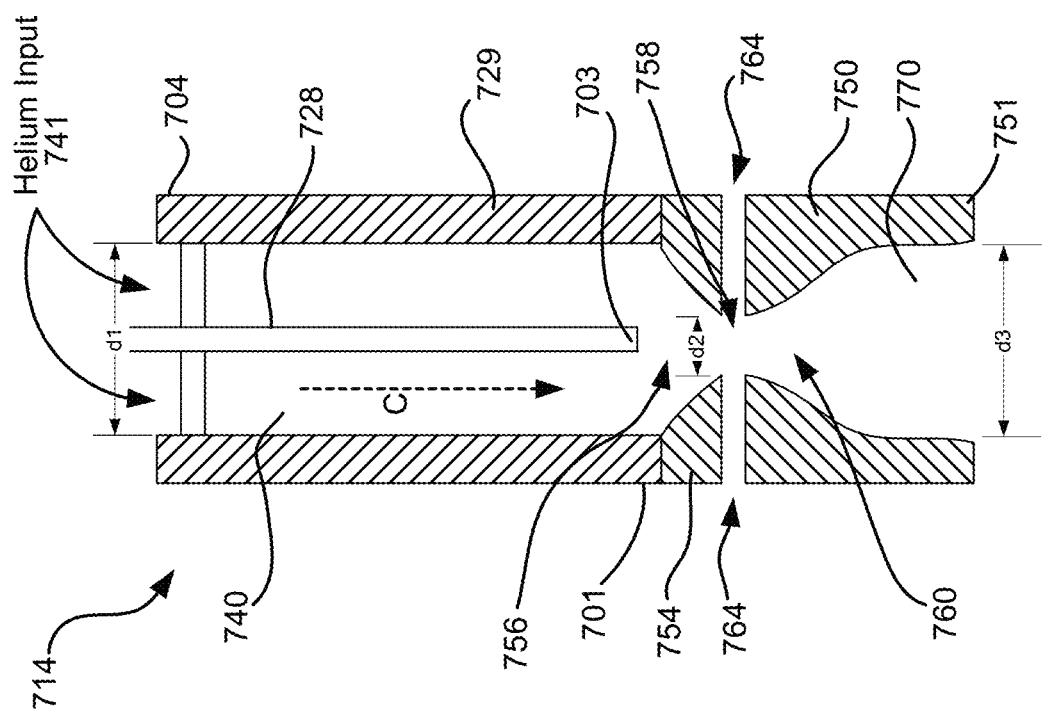
FIG. 6B is a side cross-section view of the plasma applicator of FIG. 6A.
Figure 6A:
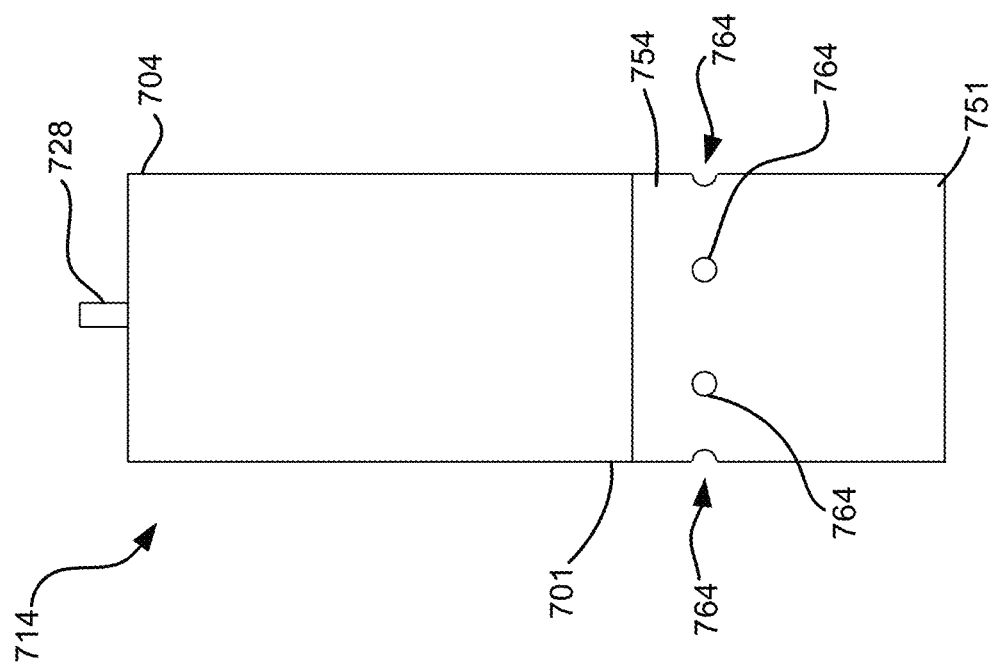
FIG. 6A is a side view a plasma applicator including a De Laval nozzle in accordance with an embodiment of the present disclosure.

Referring to FIG. 6A, a side view of an applicator 714 is shown in accordance with an embodiment the present disclosure. Referring to FIG. 6B, a side-cross-section view of the applicator 714 is shown in accordance with the present disclosure. Applicator 714 includes a fluid flow housing 729 and a De Laval nozzle 750. Housing 729 includes a distal end 701, a proximal end 704, an interior 740, and an electrode 728, where electrode 728 is centrally disposed within interior 740. Nozzle 750 includes an interior 770, and non-inert gas inputs 764, where inputs 764 provide access to the interior 770 of nozzle 750. Interior 770 of nozzle 750 includes a converting portion 756, a throttle portion 758, and a diverging portion 760. Distal end 701 of housing 729 is coupled to proximal end 754 of nozzle 750. Housing 729, nozzle 750, and electrode 728 are coaxial. It is to be appreciated that in some embodiments housing 729 and nozzle 750 may be a component. In other embodiments, housing 729 and nozzle 750 may be separate components, where nozzle 750 is configured to be an add-on component that may be coupled to housing 729.

It is to be appreciated that the cross-sectional area of both converging portion 756 and diverging portion 760 are larger than throttle portion 758. In some embodiments, the cross-sectional area of portion 756 is smaller than the cross-sectional area of portion 760.

In either case, the interior 740 of housing 729 includes a first diameter (d1, shown in FIG. 6B) remaining constant from the proximal end 704 to the distal end 701 of housing 729. Progressing from the proximal end 754 of nozzle 750, along a direction C (i.e., the direction of carrier gas flow), converging portion 756 converges toward the center of applicator 714, such that, the diameter of interior 770 is gradually reduced along direction C throughout converging portion 756. Throttle portion 758 includes a second diameter (d1, shown in FIG. 6B), where the second diameter is smaller than the first diameter. The geometry of the interior 770 of nozzle 750 is configured such that the second diameter is the smallest diameter at any point in the interior of applicator 714. Continuing along direction C, diverging portion 760 diverges away from the center of applicator 714, such that, the diameter of interior 770 is gradually increases along direction C throughout diverging portion 760 until a third diameter (d3, shown in FIG. 6B) is achieved at the distal end 751 of nozzle 750. It is to be appreciated that in some embodiments, the first diameter may be substantially the same as the third diameter, while in other embodiments, the third diameter may be larger than the first diameter.

In operation, inert gas (e.g., Helium) is provided via gas input 741 and flows through interior 740 of housing 729 along direction C. A plasma discharge beam is generated when an inert gas passes over the distal tip 703 of the electrode 728, when the electrode 728 is supplied with high voltage at a high frequency from an electrosurgical generator. The plasma discharge beam exits the distal ends 701 of fluid flow housing 729 and distal end 751 of nozzle 750.

As the plasma discharge and inert gas flow through portions 756, 758, and 760 of interior 770, a pressure difference is created between the interior 770 of nozzle 750 and the exterior of applicator 714, such that the pressure at throttle portion 758, is lower than the pressure exterior to applicator 714. The lower pressure of the throttle portion 758 causes non-inert gas from the exterior of applicator 114 to be sucked or drawn into the throttle portion 758 of interior 770 via gas inputs 764 (due to the Venturi effect described above). The non-inert gas drawn into the throttle portion 758 of interior 770 is then injected into the plasma discharge beam of applicator 714 and mixed to generate reactive species.

It is to be appreciated that in some embodiments, the non-inert gas that is drawn in through gas inputs 764 is the ambient air outside of applicator 714. In this embodiment, no additional gas supply is needed to inject non-inert gas into interior 770.

In other embodiments, a secondary gas supply may be coupled to gas inputs 764 to provide a non-inert to the interior 770 of nozzle 750. For example, a second fluid flow housing may be coaxially disposed over fluid flow housing 729, where non-inert gas is provided the interior of the second fluid flow housing and into the gas inputs 764 to be injected into interior 770. An embodiment of applicator 729 including a second fluid flow housing is shown in FIG. 6C.

Figure 6D:
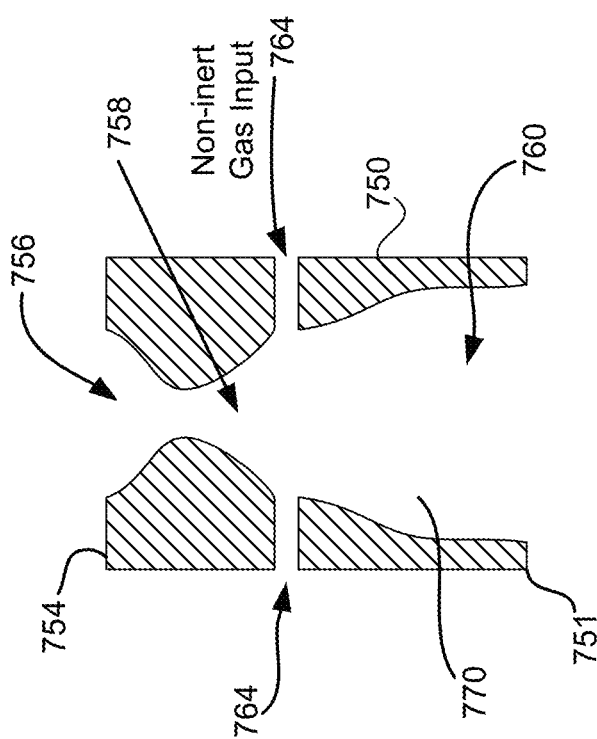
FIG. 6D illustrates an alternative De Laval nozzle in accordance with another embodiment of the present disclosure.
Figure 6C:
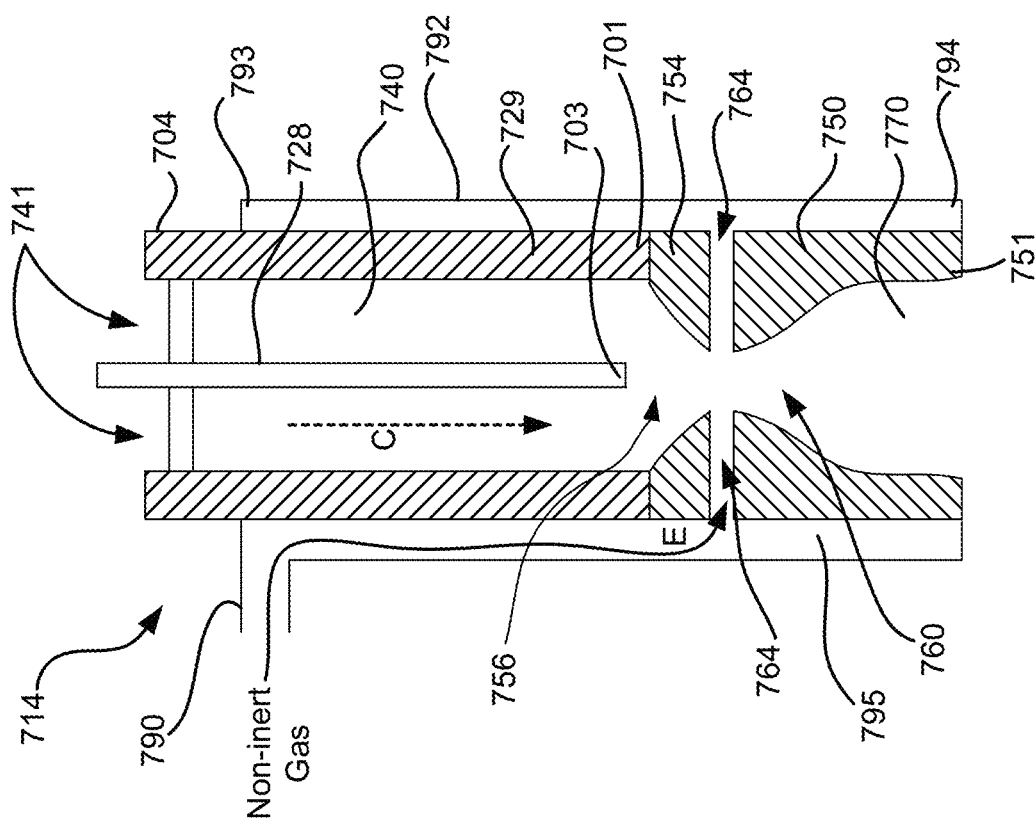
FIG. 6C is a side cross-section view of a plasma applicator include a De Laval nozzle and a secondary fluid flow housing in accordance with another embodiment of the present disclosure.

Referring to FIG. 6C, a side cross-sectional view of applicator 714 is shown with a second fluid flow housing 792 coaxially disposed over first fluid flow housing 729. Fluid flow housing 729 includes a proximal end 793, a distal end 794, and a non-inert gas input 790. Non-inert gas port or input 790 is coupled to a non-inert gas source and configured to provide non-inert gas into the interior 795 of fluid flow housing 792. In operation, as the inert carrier gas flows in a distal direction C through interior 740 of housing 729 and through interior 770 of nozzle 750. A plasma discharge beam is generated when an inert gas passes over the distal tip 703 of the electrode 728, when the electrode 728 is supplied with high voltage at a high frequency from an electrosurgical generator.

As the plasma discharge beam and inert gas flow through portions 756, 758, and 760 of interior 770, a pressure difference is created between the interior 770 of nozzle 750 and the interior 795 of fluid flow housing 792, such that the pressure at throttle portion 758, is lower than the pressure in interior 795. The lower pressure of the throttle portion 758 causes non-inert gas in the interior 795 of housing 792 to be sucked or drawn into the throttle portion 758 of interior 770 via gas inputs 764 (due to the Venturi effect described above), as indicated by arrow E in FIG. 6C. The non-inert gas drawn into the throttle portion 758 of interior 770 is then injected into the plasma discharge beam of applicator 714 and mixed to generate reactive species.

It is to be appreciated that although only four non-inert gas inputs 764 are shown in FIG. 6A, in other embodiments, more or less gas inputs 764 may be disposed around nozzle 750 at predetermined intervals as desired. Furthermore, in some embodiments, gas inputs 764 may include titled vanes (similar to vanes 149) to introduce a tangential flow (i.e., a curl or swirl) into the non-inert gas relative to the plasma discharge and inert gas flowing along direction C. It is also to be appreciated that gas input 764 may be configured to inject non-inert gas into interior 770 at various angles. For example, in FIG. 6B, gas inputs 764 are configured to be aligned perpendicularly to direction C, such that non-inert gas is injected into interior 770 in a direction perpendicular to direction C. However, in other embodiments, gas inputs 764 may be configured to be aligned at other angle relative to direction C (e.g., 45 degrees, 30 degrees, etc.), such that, non-inert gas is injected into interior 770 at any desirable angle to promote the mixing of inert and non-inert gases.

It is to be appreciated that, since the throttle portion 758 is disposed distal to the electrode tip 703, there is no risk of electrode erosion from injection of the non-inert gas into interior 770. The pressure in the converging portion 756 is always higher than the pressure in the throttle portion 758, therefore, the electrode 728 is protected from upstream (i.e., proximal) migration of the non-inert gas injected into interior 770.

Although, in the embodiment of nozzle 750 shown in FIG. 6B, gas inputs 764 are configured to inject non-inert gas into the throttle portion 758, in other embodiments of the present disclosure, gas inputs 764 may be disposed downstream (distally) of throttle portion 758 in diverging portion 760. For example, referring to FIG. 6D, gas inputs 764 are shown disposed downstream of throttle portion 758. It is to be appreciated that the placement of gas inputs 764, must be chosen such that the gas inputs 764 are placed in a portion of interior 770 that has a sufficient low pressure relative to the exterior of applicator 714 to enable the Venturi effect to occur when inert gas flows along direction C through the interior of applicator 714. Since the pressure in interior 770 is the lowest at throttle portion 756, when gas inputs 764 are placed in diverging portion 760, better pressure differentials between the interior 770 and the exterior of applicator 714 are achieved as gas inputs 764 are placed in a portion of diverging portion 760 that is closer to throttle portion 758.

It is to be appreciated that, in some embodiments, walls of the fluid flow housings 729, 792, and the nozzle 750 are made of a non-conducting material.

It is to be appreciated that, in some embodiments, the nozzle 750, described above, is generally cylindrical in shape and includes a generally cylindrical hollow interior.

It is to be appreciated that nozzle 750 may be implemented into any of the applicators described above.

Figure 7A:
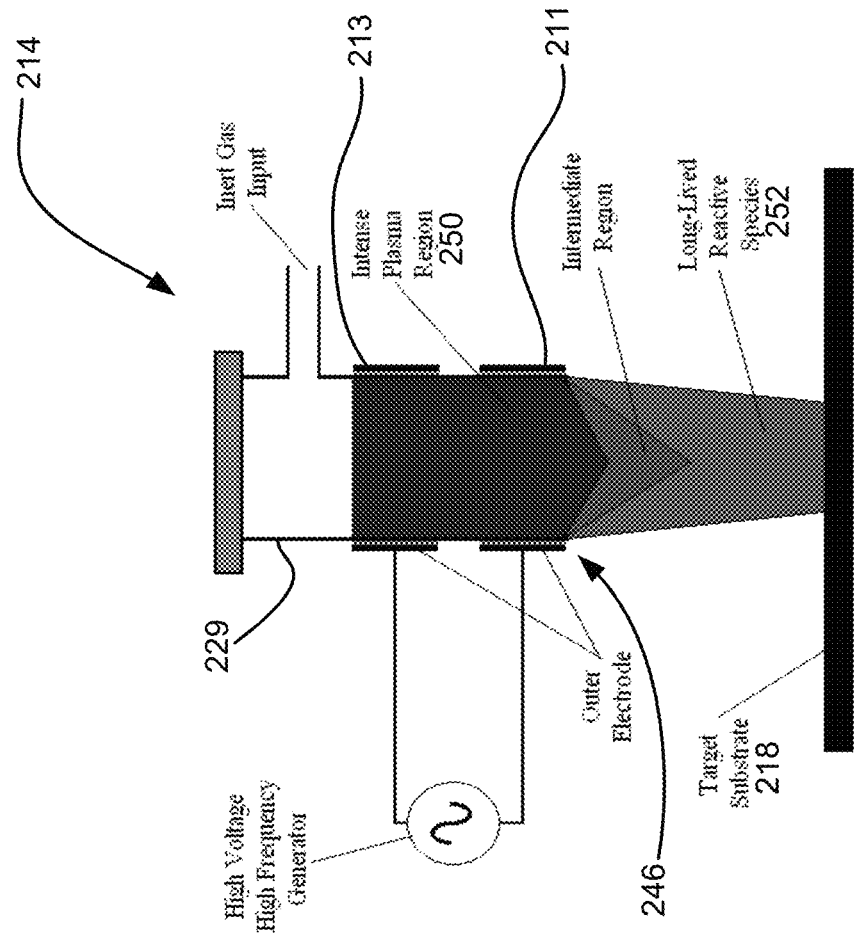
FIG. 7A illustrates a local discharge applicator with two external electrodes in accordance with an embodiment of the present disclosure.
Figure 7B:
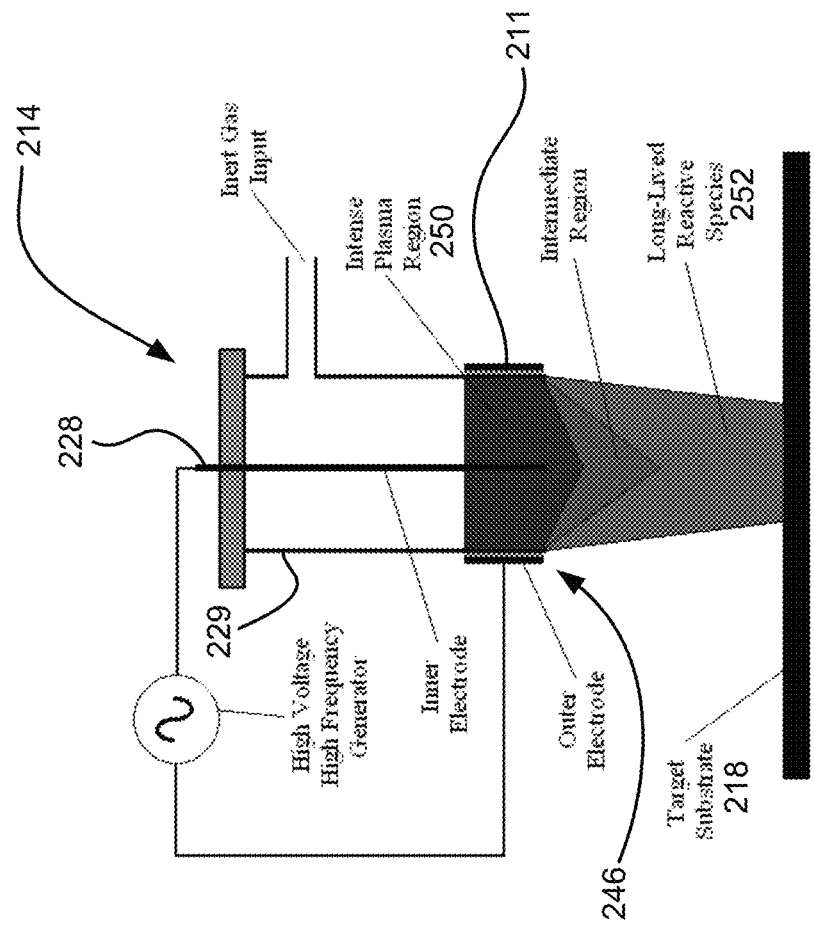
FIG. 7B illustrates a local discharge applicator with one external electrode and one internal electrode in accordance with an embodiment of the present disclosure.

Cold plasma applicator topologies can be broadly grouped into local discharge types and direct discharge types. In the local discharge topologies, an external electrode is placed around the applicator nozzle tip, i.e., the distal end of the fluid flow housing. For example, referring to FIG. 7A, a local discharge applicator 214 with two external electrodes is illustrated. A first external electrode 211 is disposed around the distal end 246 of the fluid flow housing 229. A second external electrode 213 may be placed further upstream of the first external electrode 211. Alternately, as shown in FIG. 7B, the second electrode 228 may be an internal electrode. The primary plasma discharge occurs between these electrodes (i.e., intense plasma region 250) and is said to be "local" to the applicator. An afterglow plasma (i.e., long-lived reactive species region 252) exits the applicator nozzle, and in general, carries little or no current between the applicator and the target surface 218. The target surface 218 may be either electrically conductive or non-conductive.

Figure 8:
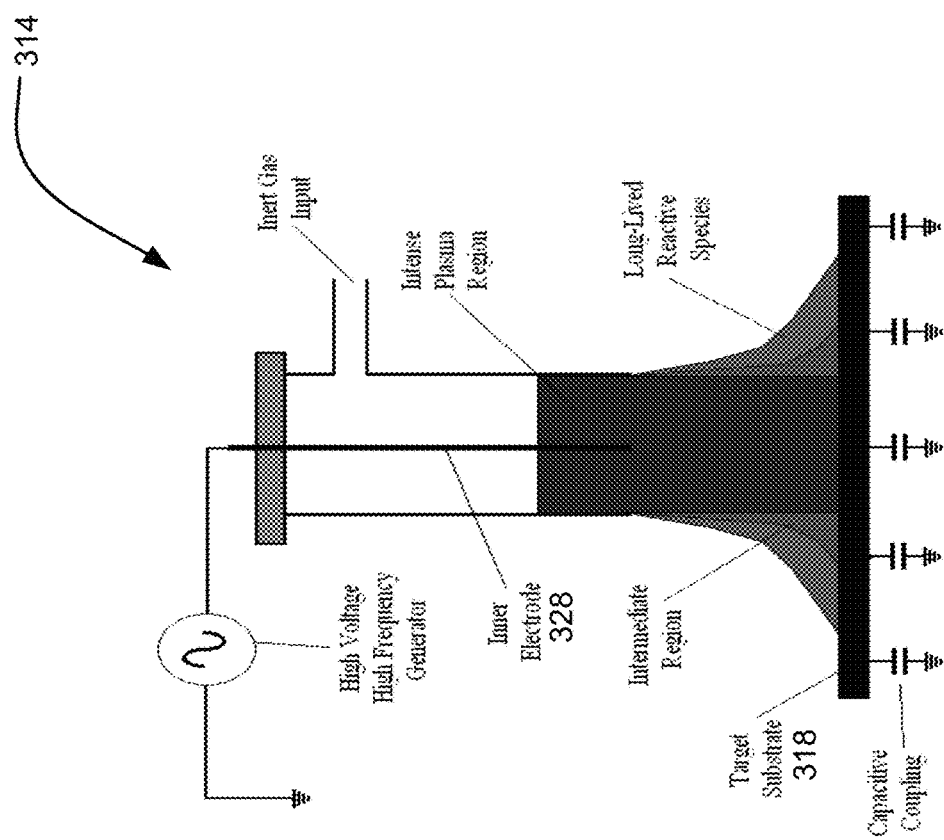
FIG. 8 illustrates a direct discharge applicator in accordance with an embodiment of the present disclosure.

By contrast, a direct discharge applicator topology only has a single internal electrode, as shown in FIG. 8. A primary direct discharge path is created between the internal electrode 328 and the conductive target surface 318. If this target surface 318 is grounded, the plasma beam carries a conduction current. If the target surface 318 is electrically isolated, the plasma beam carries a displacement current, alternately charging and discharging the target surface as though it were one plate of a capacitor.

Since a direct plasma discharge applicator topology establishes a continuous current carrying path between the applicator and the target site, the distance over which this plasma discharge may interact with surrounding gases is substantially greater than in the local discharge topology. Consequently, the rate at which radical species are generated is greater in the direct discharge topology as compared to the local discharge, all other variables being equal.

However, since the direct discharge plasma path is initiated from the tip of the applicator's internal electrode, the plasma beam diameter is generally small, on the order of one to a few millimeters. While this is beneficial for applications where high precision positioning and control are important, other applications would benefit from a wider beam, such as disinfection, sterilization, and cancer treatment, among others. A wider beam would also provide greater surface area to interact with surrounding gases, thereby further enhancing radical species production rates.

Combining topological components of both local and direct discharge permits a pre-ionization of the carrier gas stream before it approaches the tip of the internal electrode, as shown and in FIGS. 9A and 9B. Referring to FIG. 9A, applicator 414 includes a fluid flow housing 429 with a centrally disposed internal electrode 428. When an inert gas is introduced to the fluid flow housing 429 via input 440 and the electrode 428 is energized (e.g., via an electrosurgical generator or other power source), a plasma discharge beam results at the distal end 446 of the applicator 414. Upper external electrode 413 is disposed at a proximal end 431 of the fluid flow housing 429. It is to be appreciated that electrode 413 may be a ring electrode that completely surrounds the exterior of the appropriate portion of the fluid flow housing 429. By positioning the upper external electrode 413 at the proximal end 431 of the housing 429 before the distal tip 433 of electrode 428, a pre-ionization of the carrier gas stream is achieved. In this manner, when the pre-ionized carrier gas reached the tip 433, the resulting beam discharge plasma beam is wider.

FIG. 9B illustrates a further embodiment of pre-ionization of the carrier gas stream before it approaches the tip of an internal electrode of an applicator. Here, applicator 460 includes a fluid flow housing 429 with a centrally disposed internal electrode 428. When an inert gas is introduced to the fluid flow housing 429 via input 440 and the electrode 428 is energized, a plasma discharge beam results and exits at the distal end 446 of the applicator 414. Upper external electrode 413 is disposed at a proximal end 431 of the fluid flow housing 429. Lower external electrode 411 is disposed at a distal end 446 of the fluid flow housing 429. It is to be appreciated that electrodes 411, 413 may be ring electrodes that completely surround the appropriate exterior portions of the fluid flow housing 429. By positioning the upper external electrode 413 at the proximal end 431 of the housing 429 before the distal tip 433 of electrode 428, a pre-ionization of the carrier gas stream is achieved. The lower electrode 411 further contributes to the overall pre-ionization. Note that both upper and lower external electrodes, 413 and 411 respectively, must be operated at a different electrical phase relationship than that of the high voltage high frequency power being applied to the internal electrode 428 to maintain an ionizing potential between them. In this manner, when the pre-ionized carrier gas reached the tip 433, the resulting beam discharge plasma beam is wider.

It is to be appreciated that several of the embodiments described above include multi-electrode configurations (i.e., including one or more exterior electrodes and an interior electrode). Referring to FIG. 10, several phase combinations are possible to satisfy the requirement of maintaining an ionizing potential between the electrodes of the applicators provided above.

Figure 10A:
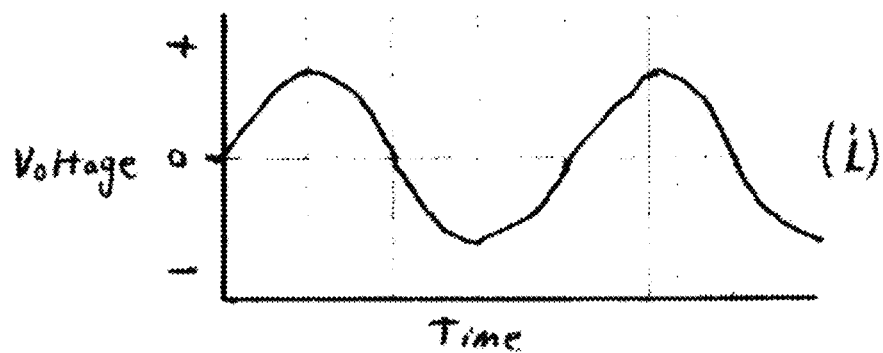
FIGS. 10A, 10B, and 10C illustrate various phase combinations for use with multi-electrode plasma applicators in accordance with an embodiment of the present disclosure.
Figure 10A:
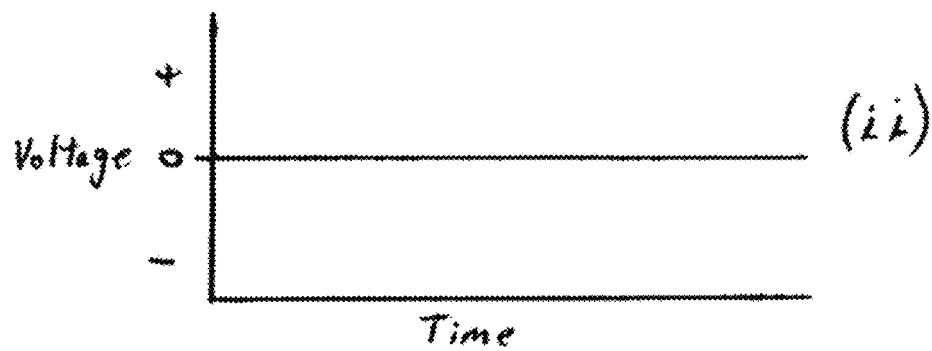

FIG. 10A includes a phase combination I, where one or more electrodes include a waveform (i) and one or more electrodes are held at ground waveform (ii). For example, for applicators including both external and internal electrodes, such as in FIGS. 7A, 7B, 9A, and 9B, the external electrodes may be held at waveform (i) and the internal electrode may be held at waveform (ii). Alternatively, the internal electrode may be held at waveform (i), while the external electrode is held at waveform (ii).

Figure 10B:
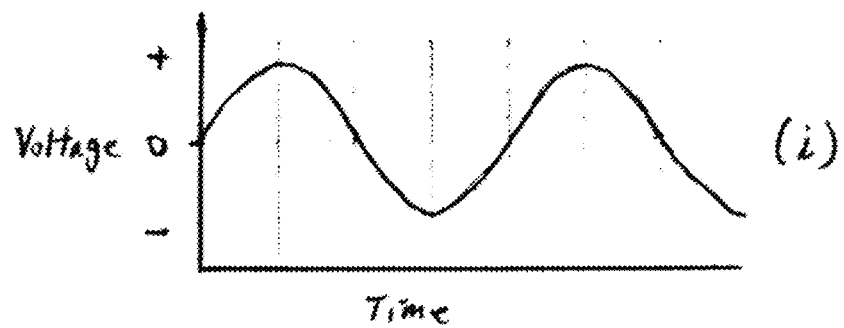
Figure 10B:
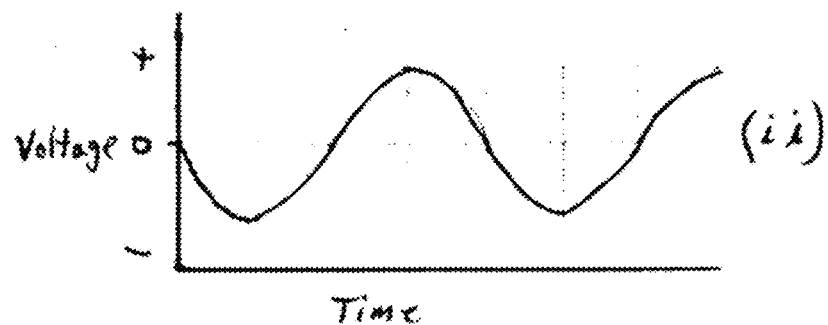

FIG. 10B includes an alternative phase: phase combination II. In phase combination II, waveforms (i) and (ii) are out of phase (e.g., by 180 degrees). As applied to the applicators of FIGS. 7A, 7B, 9A, and 9B, the external electrodes may be held at waveform (i) and the internal electrode may be held at waveform (ii). Alternatively, the internal electrode may be held at waveform (i), while the external electrode is held at waveform (ii).

Figure 10C:
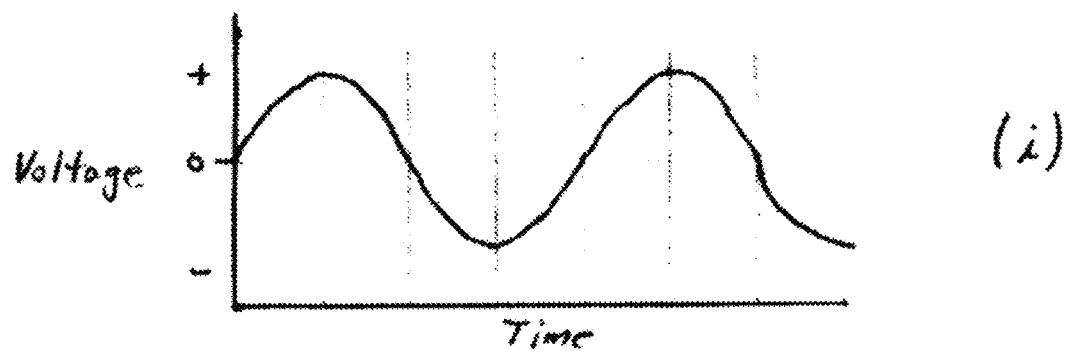
Figure 10C:
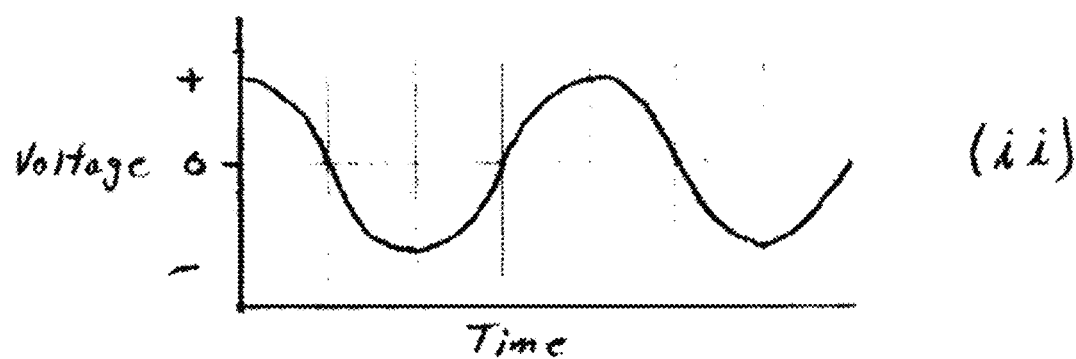
Figure 10C:
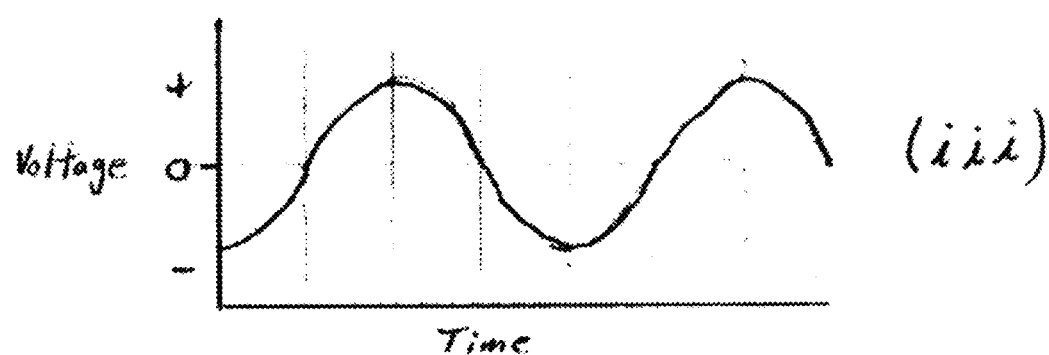

FIG. 10C includes yet another alternative phase combination: phase combination III. Phase combination III is applicable to applicators includes three electrodes, where waveforms (i), (ii), and (iii) are each out of phase (e.g., 90 degrees) relative to each other, and each waveform is applied to a separate electrode. For example, applicator 460 of FIG. 9B, includes electrodes 411, 413, and 428. Using phase combination III with applicator 460 of FIG. 9B, a different waveform of waveforms (i)-(iii) of phase combination III may be applied to each of electrodes 411, 413, 428. For example, in one embodiment, waveform (i) is applied to internal electrode 428 and waveforms (ii) and (iii) are applied to external electrodes 413 and 411 respectively.

It is to be appreciated that the waveforms shown in FIG. 10C are merely one combination of several possible combinations of waveforms that may be applied to applicators includes multiple electrodes. Any arbitrary waveform combination can be used so long as the instantaneous voltage difference between internal and external electrodes is sufficient to ionize the gas between them.

As mentioned previously, there are many applications where a highly localized effect is desirable to minimize collateral damage to surrounding tissue, and so it is also desirable to minimize electrical current flow away from the application site. Since electrical power is the product of voltage multiplied by current, decreasing the current implies a compensating increase in voltage to maintain a given applied power level. However, increasing the applicator plasma voltage carries with it a number of increasing difficulties.

There are two methods of providing high voltage high frequency power to the applicator electrode in the direct discharge configuration. One is to have a final stage high voltage transformer located in the applicator hand piece itself. For example, referring to FIG. 11, an electrosurgical apparatus 500 in accordance with another embodiment of the present disclosure is illustrated. Generally, the apparatus 500 includes a housing 502 having a proximal end 503 and a distal end 505 and a tube 504 having an open distal end 506 and a proximal end 508 coupled to the distal end 505 of the housing 502, thereby forming a handpiece. The housing 502 includes a plurality of buttons 507, e.g., buttons 514, 515 and 519, and a first slider 516 and second slider 521. Activation of the first slider 516 will expose a blade or electrode 518 at the open distal end 506 of the tube 504. Activation of the second slider 521 sets the apparatus into different modes. Activation of the individual buttons 514, 515, 519 will apply electrosurgical energy to the blade 518 to affect different electrosurgical modes and, in certain embodiments, enable gas flow through an internal flow tube (not shown). For example, in one embodiment, when the electrode 518 is retracted into the tube 504, a plasma discharge is generated when an inert gas in flowing through the internal flow tube and high voltage at high frequency is applied to the electrode 518.

Additionally, a transformer assembly 520 is provided on the proximal end 503 of the housing 502 for coupling a source of radio frequency (RF) energy to the apparatus 500 via cable 560 and connector 562. The cable 560 includes a plurality of conductors for providing electrosurgical energy to the apparatus 500 and for communication signals to and from the apparatus 500 and an RF source, e.g., an electrosurgical generator 523.

Figure 11:
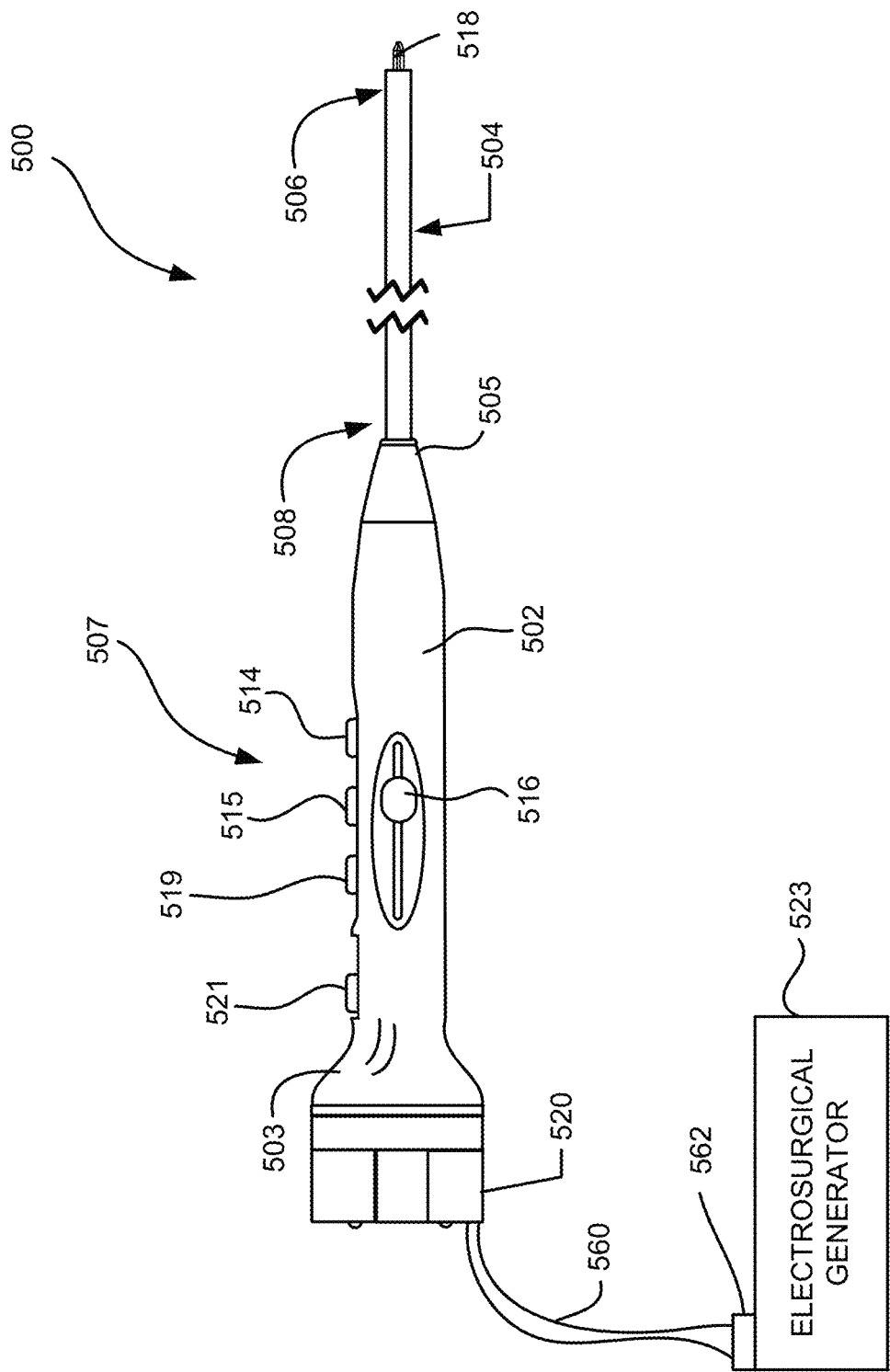
FIG. 11 illustrates an exemplary plasma apparatus in accordance with another embodiment of the present disclosure.

The high voltage output of a transformer in the transformer assembly 520 is connected to the direct discharge electrode 518 through a current limiting device, typically a high voltage capacitor or resistor. Such an applicator as shown in FIG. 11 can be unwieldy due to the increased weight of the high voltage transformer, in addition to the higher construction costs.

An alternate method is to have the final stage high voltage output transformer located in the generator box, e.g., electrosurgical generator 523, resulting in a much lighter weight, more dexterous applicator. The difficulties here are the need for a higher voltage rating for the cable connecting the applicator to the generator box, increased radiated emissions from that cable, and the need for an ionization initiating pulse with a high crest factor (ratio of peak to RMS voltage). Since the output transformer is driving the load of the cable in addition to the actual application load, there may be an undesirable increase in applied current to compensate for a decrease in voltage in providing a given power level.

An ideal situation would be to produce the final output high voltage generation in the applicator hand piece without the previous penalties of increased weight, cost and loss of dexterity. Rather than employing a single high voltage output transformer in the transformer assembly of the applicator hand piece, a series of small light weight saturable core transformers may be employed. In one embodiment, a series of saturable core transformers are disposed in, for example, the transformer assembly 520.

By saturating the core of each of the series of transformers where the secondary of the previous stage (i.e., transformer) is directly connected to the primary of the next stage, the generation of high frequency harmonics results. These harmonics add to produce a narrower pulse width of increased amplitude. A succession of stages each sequentially narrows the pulse and raises the amplitude until the final required output voltage is achieved. The degree of core saturation in each transformer stage is minimized, at the potential increase in the number of stages, to reduce parasitic power losses in the overall conversion of pulse width to pulse amplitude. Core saturation leads to the generation of waste heat, which must be effectively dissipated, and reduces overall efficiency. The more heavily saturated a core becomes, the more waste heat is generated, but the degree of pulse compressing higher harmonics is also increased. A design optimization tradeoff is made between degree of core saturation, overall conversion efficiency, and the number of stages required to produce the desired output voltage.

Figure 12:
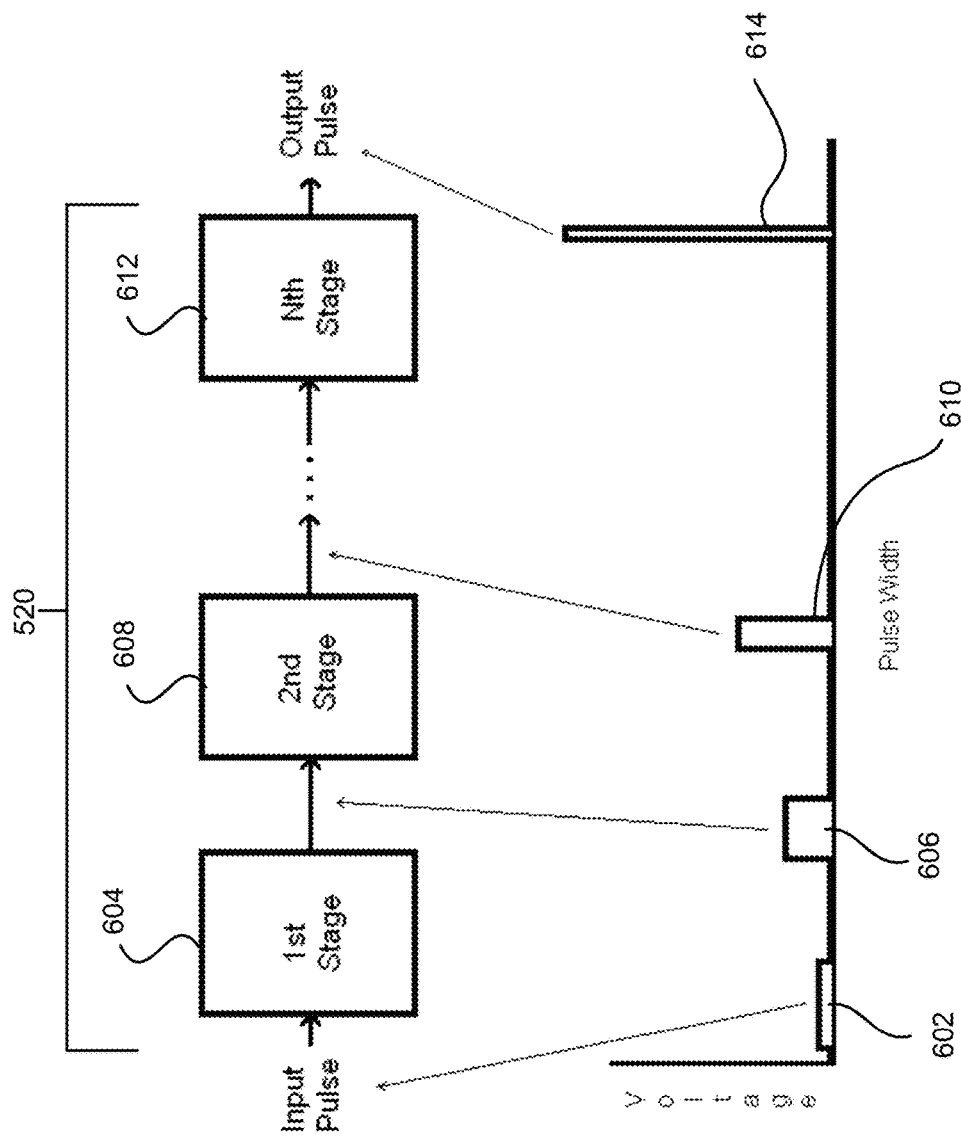
FIG. 12 illustrates a multi-stage approach to high voltage pulse generation in accordance with an embodiment of the present disclosure.

FIG. 12 illustrates the voltage pulses after each corresponding transformer or output stage. An input pulse 602 is transmitted to a first stage transformer 604. The transformed pulse 606 is illustrated as having a shorter pulse width and larger amplitude relative to pulse 602. The transformed pulse 606 is then transformed in the $2^{nd}$ stage transformer 608 resulting in pulse 610, which has a relative shorter pulse width and larger amplitude relative to pulse 606. The transformed pulse 610 is then transformed to the Nth stage transformer 612 resulting in output pulse 614, which has a relative shorter pulse width and larger amplitude relative to pulse 610. It is to be appreciated that the number of transformers may be variable. In one embodiment, the number of transformers may be dependent on a desired pulse width and amplitude of the final output pulse that is subsequently transmitted to the electrode, e.g., electrode 518. For example, if a given stage has a pulse compression ratio of 4 (output pulse width is ¼ the input pulse width) then the amplitude will increase approximately 4 times. Two successive stages will increase the amplitude 16 times, and three stages will increase it 64 times. A 100 volt peak pulse at the input to a series of three stages will become a 6.4 kV peak output pulse.

Figure 13:
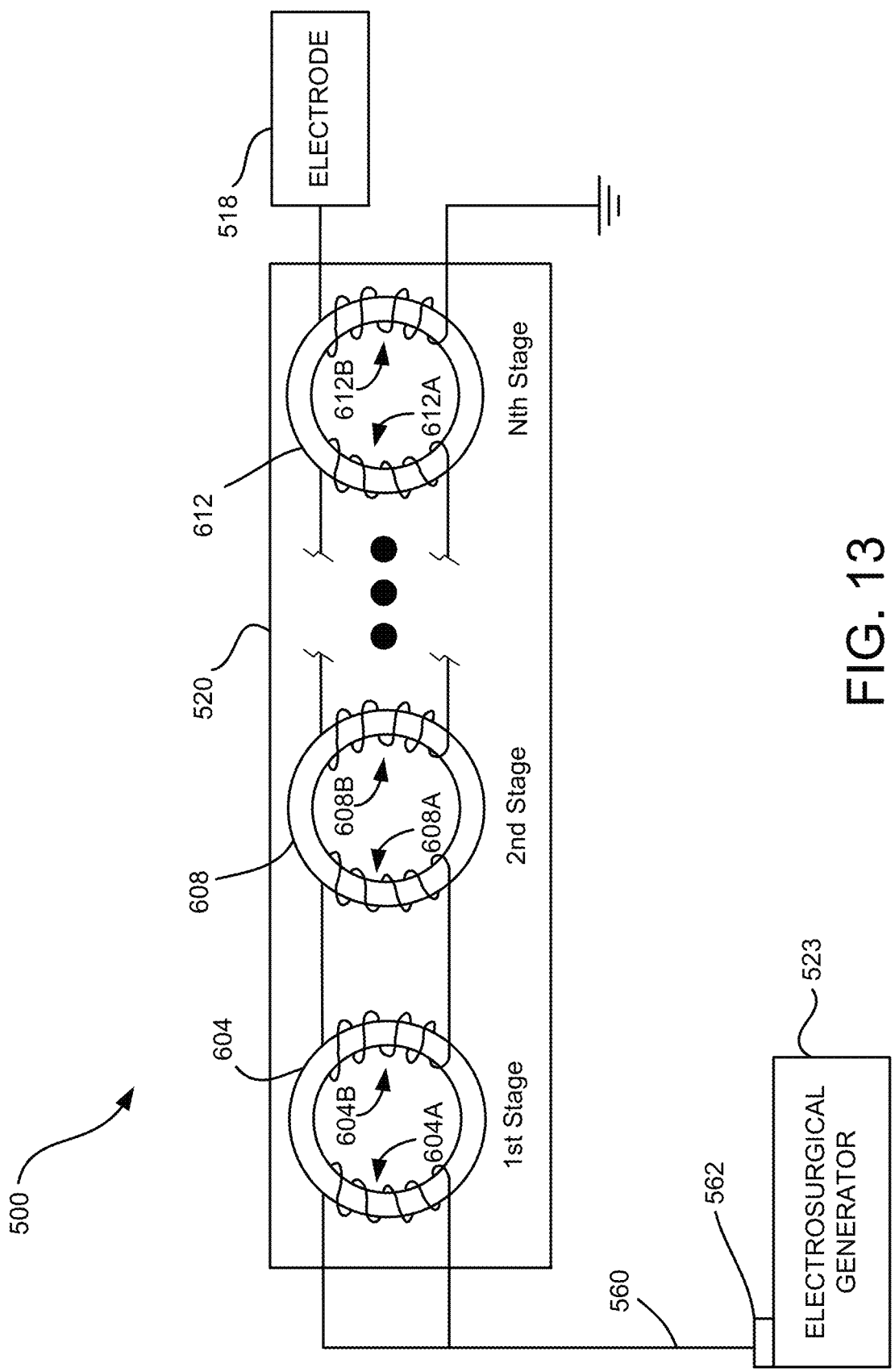
FIG. 13 illustrates the plasma apparatus of FIG. 11 with a transformer assembly including multiple serially coupled saturable core transformer in accordance with an embodiment of the present disclosure.

Referring to FIG. 13, electrosurgical apparatus 500 is shown with transformer assembly 520 including a plurality of saturable core transformers coupled serially. As shown in FIG. 13, each transformer includes a ring-shaped core, where a primary winding is wrapped around a first side or portion of the ring-shaped core and a secondary winding is wrapped around a second side or portion of the ring-shaped core. It is to be appreciated that each ring-shaped core is made of a ferrite material, for example, comprising manganese and/or zinc. Exemplary ring-shaped core materials that may be used for the cores of each transformer of transformer assembly 520, include, but are not limited to, Magnetics Corp. Type 3B7, Magnetics Corp. Type N-29, and METGLAS® Magnetic Alloy 2714. It is to be appreciated that the primary winding and secondary winding of each transformer may include a predetermined number of turns. For example, in one embodiment, the primary and secondary of each transformer of assembly 520 includes 10 turns.

As shown in FIG. 13, transformer assembly 520 includes a plurality of saturable core ring transforms 604, 608, 612. Electrosurgical generator 523 is coupled to the primary 604A of a first transformer 604 via cable 560. The secondary 604B of transformer 604 is coupled to the primary 608A of a second transformer 608 and the secondary 608B of the second transformer 608 is coupled to the primary of a subsequent transformer. This manner of serial coupling between each saturable core transformer in assembly 520 continues until the primary 612A of the last transformer 612 in assembly 520 is coupled to. The secondary 612B of the last transformer 612 is coupled to electrode 518 and to ground.

It is to be appreciated that, although only three transformers 604, 608, 612 are shown in FIG. 13 as being included in assembly 520, any number of transformers may be included in assembly 520 to achieve the desired peak voltage. In one embodiment, four transformers are included in assembly 520, however, in other embodiments more or less transformers may be included. Furthermore, it is to be appreciated that, in some embodiments, each transformer included in assembly 520 is substantially identical (i.e., the same component), while in other embodiments, the value and/or properties of each transformer in assembly 520 may be different to optimize the functioning of transformer assembly 520.

In one embodiment, each stage or transformer in assembly 520 is arranged in a substantially linear fashion (i.e., in a straight line). This linear arrangement provides physical high voltage isolation between each stage or transformer.

In operation, electrosurgical energy, in the form of a pulse train, is provided to the input of transformer assembly 520 and received by the primary 604A of the $1^{st}$ stage or transformer 604. The width of each pulse received by the $1^{st}$ stage or transformer 604 is narrowed, while the amplitude of the pulse is increased, as described above. The output of the $1^{st}$ stage is provided via the secondary 604B of the 1st stage 604 to the primary 608A of the $2^{nd}$ stage 608, where the $2^{nd}$ stage 608 is also configured to narrow the width and increase the amplitude of the received pulse. The output of the $2^{nd}$ stage 608 is then provided via the secondary 608B of the $2^{nd}$ stage 608 to the primary of the next stage in transformer assembly 520. This process is repeated by each stage in transformer assembly 520, until the last stage 612 outputs a final pulse via the secondary 612B of the last stage 612, which is outputted via the output of transformer assembly 520 to electrode 518.

It is to be appreciated that the transformer assembly 520 shown in FIGS. 11, 12, and 13 may be included and incorporated into any of applicators 114, 214, 314, 414, 460, 714, and/or 500 described above. It is to be appreciated that the pulse compression technique employed in transformer assembly 520, may be implemented with applicators including both internal and external electrodes. Where two phase combinations are required, i.e., as provided for by FIGS. 10A and 10B, for example, with applicators including two electrodes, a first end of the secondary of the last transformer 612 in assembly 520 is coupled to the first electrode of the applicator and a second end of the secondary of the last transformer 612 is coupled to the second electrode of the applicator. Where two or more phase combinations are required, i.e., as provided for by FIGS. 10A-C, the timing of the various pulses must satisfy the requirement that sufficient voltage exists between the electrodes of the applicator to ionize the gas between them, and a separate transformer assembly may be needed for each phase. For example, where two or more phase combinations are required (i.e., where two or more electrodes are included in the applicator), a second and/or third group of serially coupled transformers may be included in assembly 520 to be coupled to a second and/or third electrode of the applicator.

It is to be appreciated that, in some embodiments, the fluid flow housings of each of the applicators described above are generally cylindrical in shape and include a generally cylindrical hollow interior.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure as defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. An electrosurgical apparatus comprising:
   a first fluid flow housing including a proximal end, a distal end, a first gas port, and a hollow interior, the first gas port configured to provide a first gas to the hollow interior, such that, the first gas flows through the hollow interior and is provided to the distal end of the first fluid flow housing;
   a second fluid flow housing including a proximal end, a distal end, a second gas port, and a hollow interior, the second fluid flow housing coaxially disposed over the first fluid flow housing, the second gas port configured to provide a second gas to the hollow interior of the second fluid flow housing, such that, the second gas flows through the hollow interior and is provided to the distal end of the second fluid flow housing; and
   an electrode disposed through the hollow interior of the first fluid flow housing, the electrode including a distal tip and configured to receive electrosurgical energy from an electrosurgical generator, such that, when the first gas passes over the distal tip of the electrode and the electrode receives electrosurgical energy, the first gas is at least partially ionized to generate a plasma discharge beam, the plasma discharge beam exiting the distal end of the first fluid flow housing,
   wherein the distal end of the first fluid flow housing extends past the distal tip of the electrode and the distal end of the second fluid flow housing is configured to inject the second gas into the plasma discharge beam in a direction perpendicular to a direction of flow of the first gas beyond the distal end of the first fluid flow housing.

2. The electrosurgical apparatus of claim 1, wherein the distal end of the second fluid flow housing includes a gas output that extends in the direction perpendicular to the direction of flow of the first gas.

3. The electrosurgical apparatus of claim 2, wherein the gas output is configured as a circular slot that injects the second gas radially inwards into the plasma discharge beam.

4. The electrosurgical apparatus of claim 2, wherein the distal end of the second fluid flow housing includes at least one inlet vane that is downstream of the electrode, the at least one inlet vane configured to provide a tangential flow to the second gas as the second gas is injected and mixed into the plasma discharge beam.

5. The electrosurgical apparatus of claim 1, wherein the distal end of the second fluid flow housing includes a tapered tip, the tapered tip configured to increase the exit velocity of the second gas.

6. The electrosurgical apparatus of claim 5, wherein the tapered tip is configured in a conical shape.

7. The electrosurgical apparatus of claim 6, wherein the tapered tip is removably coupled to the second fluid flow housing.

8. The electrosurgical apparatus of claim 1, further comprising a transformer assembly, the transformer assembly including a plurality of transformers coupled in series, the transformer assembly configured to receive an input pulse from the electrosurgical generator and output an output pulse, the input pulse having a first voltage and a first pulse width and the output pulse having a second voltage and a second pulse width, the second voltage being higher than the first voltage and the second pulse width being narrower than the first pulse width.

9. The electrosurgical apparatus of claim 1, wherein the first gas is an inert gas and the second gas is a non-inert gas.

10. The electrosurgical apparatus of claim 1, wherein the first gas is helium.

11. The electrosurgical apparatus of claim 1, wherein the second gas is at least one of oxygen and/or nitrogen.

12. The electrosurgical apparatus of claim 1, wherein the second gas is a combination of oxygen and nitrogen.

13. The electrosurgical apparatus of claim 1, wherein the first gas is a combination of helium and at least one of argon, krypton and/or xenon.

14. The electrosurgical apparatus of claim 1, wherein the distal end of the second fluid flow housing is configured as a tapered tip.

15. The electrosurgical apparatus of claim 14, wherein the tapered tip is configured in a conical shape.

* * * * *